US010350244B2

(12) United States Patent
Gasser et al.

(10) Patent No.: US 10,350,244 B2
(45) Date of Patent: Jul. 16, 2019

(54) PHARMACEUTICAL COMPOSITION FOR THE TREATMENT OF DISEASES IN WHICH LPS- AND/OR APOPTOSIS REGULATION IS DISTURBED

(71) Applicants: Martin Gasser, Würzburg (DE); Ana Maria Waaga-Gasser, Würzburg (DE)

(72) Inventors: Martin Gasser, Würzburg (DE); Reinhard Lissner, Weilbach (DE); Ana Maria Waaga-Gasser, Würzburg (DE); Georg Wolz, Geisenheim (DE)

(73) Assignees: Martin Gasser, Würzburg (DE); Ana Maria Waaga-Gasser, Würzburg (DE)

( * ) Notice: Subject to any disclaimer, the term of this patent is extended or adjusted under 35 U.S.C. 154(b) by 322 days.

(21) Appl. No.: 15/100,730

(22) PCT Filed: Dec. 2, 2013

(86) PCT No.: PCT/EP2013/075287
§ 371 (c)(1),
(2) Date: Jun. 21, 2016

(87) PCT Pub. No.: WO2015/081982
PCT Pub. Date: Jun. 11, 2015

(65) Prior Publication Data
US 2016/0296567 A1 Oct. 13, 2016

(51) Int. Cl.
A61K 36/00 (2006.01)
A61K 35/20 (2006.01)
A61K 31/593 (2006.01)
A61K 9/14 (2006.01)

(52) U.S. Cl.
CPC ............... A61K 35/20 (2013.01); A61K 9/14 (2013.01); A61K 31/593 (2013.01)

(58) Field of Classification Search
CPC .................................................... A61K 36/00
USPC ....................................................... 424/725
See application file for complete search history.

(56) References Cited

U.S. PATENT DOCUMENTS

2010/0092497 A1   4/2010  Kanwar et al.

FOREIGN PATENT DOCUMENTS

| CN | 101537174 A | 9/2009 |
| CN | 101700074 A | 5/2010 |
| CN | 102239921 A | 11/2011 |
| CN | 102763729 | * 11/2012 |
| CN | 102763729 A | 11/2012 |
| WO | 9800149 A1 | 1/1998 |
| WO | 2008140335 A2 | 5/2008 |
| WO | 2008079030 A1 | 7/2008 |
| WO | 2015081982 A1 | 6/2015 |

OTHER PUBLICATIONS

"Interim Guidance for Human and Veterinary Drug Products and Biologicals", Jul. 15, 1991, U.S. Department of Health & Human Services, FDA, pp. 1-2.
Pietschmann, et al., "Bedeutung von Vitamin D im Immunsystem", J. Miner. Stoftwechs 2003; 10(3); pp. 13-15.
Bölke, E., et al.: "Preoperative Oral Application of Immunoglobulin-Enriched Colostrum Milk and Mediator Response During Abdominal Surgery," SHOCK, 2002, pp. 9-12, vol. 17, No. 1.
Cesarone, M., et al: "Prevention of Influenza Episodes with Colostrum Compared with Vaccination in Healthy and High-Risk Cardiovascular Subjects: The Epidemiologic Study in San Valentino," Clinical and Applied Thrombosis/Hemostasis, Apr. 2007, pp. 130-136, vol. 13, No. 2.
Fitzal, F., et al.: "Immunoglobulin Enriched Colostral Milk Reduces Gut-Derived Endotoxemia in a Rat Hemorrhage Model", European Journal of Trauma, 2001, No. 5, pp. 257-263.
Haussler, M., et al.: "Vitamin D receptor: molecular signaling and actions of nutritional ligands in disease prevention", Nutrition Reviews, 2008, vol. 66 (Suppl. 2), pp. S98-S112.
Lissner, R., et al: "Antibody reactivity and fecal recovery of bovine immunoglobulins following oral administration of a colostrum concentrate from cows (Lactobin) to healthy volunteers," International Journal of Clinical Pharmacology and Theropeutics, 1998, vol. 36, No. 5, pp. 239-245.
Manson, J., et al.: "Vitamin D and prevention of Cancer—Ready for Prime Time?", The New England Journal of Medicine, Apr. 2011, 364;15, pp. 1385-1387.
Park, J., et al.: "An antimicrobial protein, lactoferrin exists in the sweat: proteomic analysis of sweat," Experimental Dermatology, 2011, 20, pp. 367-376.
Roos, N., et al: "15N-labeled Immunoglobulins from Bovine Colostrum Are Partially Resistant to Digestion in Human Intestine," The Journal of Nutrition, 125, 1995, pp. 1238-1244.
Schupp, N., et al.: "Rosuvastatin protects against oxidative stress and DNA damage in vitro upregulation of glutathione synthesis," Atherosclerosis 199, 2008, pp. 278-287.
Stubbins, R., et al.: "Using components of the vitamin D pathway to prevent and treat colon cancer," Nutrition Reviews, 2012, vol. 70(12), pp. 721-729.
Uruakpa, F.O., et al.: "Colostrum and its benefits: a review," Nutrition Research, 22, 2002, pp. 755-767.
Waaga-Gasser, A.M., et al.: "Oral immunoglobulin induces mononuclear cell apoptosis in patients suffering from idiopathic chronic pain syndrome: Results from a Pilot Study," International Journal of Clinical Pharmacology, 2009, pp. 421-433, vol. 47, No. 7.
Struff, W.G., et al.: "Bovine colostrum as a biologic in clinical medicine: A review—Part II," International Journal of Clinical Pharmacology and Therapeutics, 2008, pp. 211-225, vol. 46, No. 5.
Struff, W.G., et al.: "Bovine colostrum as a biologic in clinical medicine: A review", International Journal of Clinical Pharmacology and Therapeutics, 2007, pp. 193-202, vol. 45, No. 4.
Tacket, C., et al: "Efficacy of Bovine Milk Immunoglobulin Concentrate in Preventing Illness After Shigella Flexneri Challenge," The American Society of Tropical Medicine and Hygiene, 1992, pp. 276-283, vol. 47, No. 3.
Harmsen, M., et al: "Antiviral Effects of Plasma and Milk Proteins: Lactoferrin Shows Potent Activity against both Human Immunodeficiency Virus and Human Cytomegalovirus Replication in Vitro," The Journal of Infectious Diseases, 1995, pp. 380-388, 172.

(Continued)

Primary Examiner — Michael V Meller
(74) Attorney, Agent, or Firm — Cahn & Samuels, LLP

(57) ABSTRACT

A pharmaceutical composition for the treatment of diseases in which LPS- and/or apoptosis regulation is disturbed includes colostrum and vitamin D.

6 Claims, 16 Drawing Sheets

(56) References Cited

OTHER PUBLICATIONS

"Guideline on Validation of the Limulus Amebocyte Lysate Test as an End-Product Endotoxin Test for Human and Animal Parenteral Drugs, Biological Products, and Medical Devices", Center for Drug Evaluation and Research et al., U.S. Department of Health and Human Services, Food and Drug Administration, Dec. 1987, pp. 1-54.
Huppertz, H., et al.: "Bovine Colostrum Ameliorates Diarrhea in Infection with Diarrheagenic Escherichia coli, Shiga Toxin-Producing *E. coli* and *E. coli* Expressing Intimin and Hemolysin," Journal of Pediatric Gastroenterology and Nutrition, Oct. 1999, pp. 452-456, vol. 29, No. 4.
International Preliminary Report on Patentability dated Jun. 2, 2016.
Keech, A., "Peptide Immunotherapy—Colostrum—A Physician's Reference Guide", AKS Publishing, pp. 7-8, 79, 2010.
Jenab et al., "Association between pre-diagnostic circulating vitamin D concentration and risk of colorectal cancer in European populations: a nested case-control study", BMJ Research, pp. 1-10, 2010.
Abstract of "Bovine powder for pregnant woman comprises (in weight ratio/dose) bovine (1), folic acid (0.10 to −0.15 mg), vitamin A (250-350) and vitamin D (35-50 mu g)", XP-002728159.
"Bacterial Endotoxins Test", Interim Revision Announcement, U.S. Pharmacopeia, 25th Revision, pp. 1-5, 2011.
English Abstract of CN 102763729.
English Abstract of CN 102239921.
English Abstract of CN 101537174.
English Abstract of CN 101700074.
English translation of International Preliminary Report on Patenability, dated Jun. 2, 2016.

\* cited by examiner

PHARMACEUTICAL COMPOSITION FOR THE TREATMENT OF DISEASES IN WHICH LPS- AND/OR APOPTOSIS REGULATION IS DISTURBED

This patent application is a U.S. national stage application of PCT international application PCT/EP2013/075287 filed on 2 Dec. 2013, the entirety of which is incorporated herein by reference.

FIELD OF THE INVENTION

The invention relates to a pharmaceutical composition for the treatment of diseases in which LPS and/or apoptosis regulation is disturbed.

BACKGROUND OF THE INVENTION

Colostrum (Latin: colostrum) is the first milk for mammals, which is produced by numerous mammalian species before childbirth for optimal feeding of the newborn during the first few days. It is also referred to as premilk, colostral milk, beestings or beastings (both in the case of cows) or first milk and consists of, inter alia, proteins, enzymes, vitamins, minerals, growth factors, amino acids and antibodies. By this means, the strengthening and the immune defense of the young animal or the child is supported or surrogated as a special form of loan immunity until an inherent immune system has been established after a few days to weeks.

Cow colostrum is considered to be a healthy foodstuff. There are numerous studies in relation to the effectiveness of colostrum. Colostrum is said to provide, inter alia, a certain level of protection against infectious diseases (Cesarone, et al.: Prevention of influenza episodes with colostrum compared with vaccination in healthy and high-risk cardiovascular subjects: The epidemiologic study in San Valentino: Clinical and Applied Thrombosis/Hemostasis 13(2)/2007, pp. 130-136; Tacket et al.: Efficacy of bovine milk immunoglobulin concentrate in preventing illness after *Shigella flexneri* challenge: American Journal Tropical Medicine Hygiene 47(3)/1992, pp. 276-83; Huppertz et al.: Bovine colostrum ameliorates diarrhea in infection with diarrheogenic *E. coli*, Shiga toxin-producing *E. coli* and *E. coli* expressing intimin and hemolysin: J Ped Gastroenterol Nutr 29: 452-456/1999) and support wound healing and also the regeneration of damaged intestinal mucosa (Uruakpa et al.: Colostrum and its benefits: a review: Nutrition Research 22/2002, pp. 755-67). Colostrum is also used for the cotreatment of allergies, high blood pressure, diabetes mellitus and depressions. However, there is so far a lack of evidence for the effectiveness of use in these indications.

Cholecalciferol, vitamin D3, is the vitamin D which occurs physiologically in all nonplant eukaryotes. It is formed in the body in the skin from 7-dehydrocholesterol with the aid of ultraviolet light (UVB).

In food, it occurs especially in oily fish (in contrast to the group of varieties relatively low in fat that are called whitefish in fishery, such as cod or haddock, oily fish refers to edible fish, in the muscle tissue of which fat exceeds a proportion of about two percent; depending on the species, said proportion can be over 30 percent. Examples of known species are herring, sprat, sardine and anchovy, salmon, mackerel, tuna, eel and carp. Because of their content of omega-3 fatty acids, sea-living oily fish are considered to be nutritionally and physiologically valuable) or is added as food supplement to foodstuffs. It acts as a prohormone in the body and is converted to the hormone calcitriol via an intermediate stage.

Calcitriol, also called 1α,25-dihydroxycholecalciferol (1α,25-dihydroxyvitamin D3) or 1,25(OH)$_2$D3 for short, is a highly potent secosteroid with structural similarity to the steroid hormones. It is—as explained—the physiologically active form of the prohormone vitamin D3. It is hydroxylated from 25-hydroxyvitamin D3 by means of the 1α-hydroxylase especially in the kidneys, but also in other tissues, or prescribed as medicament in rare cases. Calcitriol is bound to an intracellular receptor protein, the vitamin D receptor (VDR), and transported into the cell nucleus. There, the vitamin/receptor complex associates to the DNA and alters the transcription of various hormone-sensitive genes, ultimately leading to changes in protein synthesis with corresponding biological effects.

Vitamin D has, inter alia, an important role to play in blood calcium level regulation and in bone formation. In the medium term, a deficiency of vitamin D leads to various diseases, for example rickets or osteomalacia.

Lactoferrin (more precisely: lactotransferrin; from the Latin lacteus (milk), ferrum (iron) and transferre (to carry across)) is a protein which occurs in mammals and has multifunctional enzyme activities.

Lactoferrin belongs to the protein family of transferrins. Transferrins do not occur only in mammals; homologous genes are also found in other vertebrates and invertebrates.

Lactoferrin can be found in many body fluids of mammals, in the milk, tears, saliva, sweat, vaginal secretion, seminal plasma, nasal and bronchial secretion thereof and also other secretions thereof. In addition, it is located in white blood cells.

Lactoferrin has both antiviral (Harmsen, Martin C. et al.: Antiviral effects of plasma and milk proteins: lactoferrin shows potent activity against both human immunodeficiency virus and human cytomegalovirus replication in vitro. Journal of Infectious Diseases, Vol. 172, No. 2, 1995, pages 380-388) and antimicrobial (Park, Ji-Hye et al.: An antimicrobial protein, lactoferrin exists in the sweat: proteomic analysis of sweat. Experimental Dermatology, Vol. 20, No. 4, 2011, pages 369-371) properties. It acts not only as a peptidase (cleavage of peptides), which is why it is assigned to the group of the serine proteases, but also as an iron-binding protein—similar to transferrin—and additionally exhibits deoxyribonuclease and ribonuclease activities, whereby it is classed with the nucleases (EC 3.1.21.1). In addition, it is a strong inhibitor for tryptase.

One liter of cow's milk contains approx. 0.1 g of lactoferrin. It is saturated with iron only to a small proportion and can bind more than five times its original iron load.

Industrially, it is isolated from milk and whey. It is used in baby food and sports food, and also in cosmetics, chewing gums and functional foods.

The organism uses lactoferrin, inter alia, to deplete bacteria of iron, which is necessary for life. Since bacteria have an essential dependence on iron, the depletion of iron has an antibacterial effect. As a protease, lactoferrin is capable of destroying two or more proteins of the pathogen *Haemophilus influenzae* that are important for colonization. In addition, it compromises the type III secretion system in *Shigella* and pathogenic *Escherichia coli*. Released by leukocytes, it is thus also part of the immune system.

Colostrum or colostrum preparations are supplied commercially in a variety of ways and processed forms. For example, colostrum preparations are commercially available as liquid, in capsule form, as Colobons or as skin balm.

One supplier of colostrum preparations is the company Dr. Wolz Zell GmbH, Marienthaler Strasse 3, 65366 Geisenheim (www.wolz.de), which supplies a colostrum preparation in powder form under the brand name Lactobin® N.

In the case of said Lactobin® N or its bioequivalent precursor preparation Lactobin® Biotest, it has been known for some time that the antibody specifications which occur in the preparations act against bacterial lipopolysaccharides.

These findings of the use of Lactobin® N led to preclinical and clinical studies which have been described in two review publications by W. Struff and G. Sprotte (W. G. Struff and G. Sprotte: Bovine colostrum as a biologic in clinical medicine: a review. International Journal of Clinical Pharmacology and Therapeutics, Vol. 45—No. 4/2007 (193-202); W. G. Struff and G. Sprotte: Bovine colostrum as a biologic in clinical medicine: a review—Part II: International Journal of Clinical Pharmacology and Therapeutics, Vol. 46—No. 5/2008 (211-225).

On the basis of an incidental finding by G. Sprotte with regard to disturbed apoptosis functions of mononuclear cells in the blood of patients suffering from chronically recurring pain, patients were successfully treated during and also beyond their typical episode of pain, whereby the causal relationship between development of pain and elimination of pain by means of Lactobin® N was recognized as related to the apoptosis function normalized by the administration of the preparation (A. M. Waaga-Gasser et al.: Oral immunoglobulin induces mononuclear cell apoptosis in patients suffering from idiopathic chronic pain syndrome: results from a pilot study. International Journal of Clinical Pharmacology and Therapeutics, Vol. 47—No. 7/2009 (421-433).

Proinflammatory cytokines in the examined peripheral blood were noticeably elevated during an episode of pain, whereas anti-inflammatory cytokine profiles were measured as lowered. Treatment with Lactobin® N led to the reversal of these profiles, with the simultaneous reoccurrence of pain in the case of a deliberately effected drug holiday. The additionally determined serum level of insulin-like growth factor I (IGF I), too, was found to be significantly elevated in the treatment-free phase and dropped to the normal level with Lactobin® N. This phenomenon too is unambiguously seen by the investigators in connection with apoptosis dysfunction and the development of pain and the relief of pain with Lactobin® N. A similar finding of an extraintestinal remote effect of the colostrum preparation on other body compartments had been observed for the first time in a clinical study with the precursor preparation (Lactobin® Biotest); in this respect, there was a significant lowering of the peripherally elevated LPS level (in comparison with the placebo group) in serum when treating abdominal surgery patients (Edwin Bölke et al.: PREOPERATIVE ORAL APPLICATION OF IMMUNOGLOBULIN-ENRICHED COLOSTRUM MILK AND MEDIATOR RESPONSE DURING ABDOMINAL SURGERY. SHOCK, Vol. 17, No. 1, pp. 9-12, 2002).

Furthermore, in many patients with diverse tumor entities, there is a disturbance in the apoptosis in immunocompetent cells, representing a significant underlying problem in the case of a progressive tumor disease. The intensified downfall of immune cells is maintained by a dysregulation of LPS-triggered, chronically elevated inflammatory processes (chronic inflammation). In relation to this, relevant pathophysiological findings have only recently become available and have been substantiated especially by the research into toll-like receptors (TLR). In this connection, reference is made to the preclinical experimental results from Fitzal et al. (Florian Fitzal et al.: Immunoglobulin Enriched Colostral Milk Reduces Gut-Derived Endotoxemia in a Rat Hemorrhage Model. European Journal of Trauma, 2001, pp. 257-263) and the already mentioned results of the clinical phase II study with Lactobin® N (Edwin Bölke et al.: PREOPERATIVE ORAL APPLICATION OF IMMUNOGLOBULIN-ENRICHED COLOSTRUM MILK AND MEDIATOR RESPONSE DURING ABDOMINAL SURGERY. SHOCK, Vol. 17, No. 1, pp. 9-12, 2002). These findings suggest that the colostrum preparation, as a result of intraenteral LPS neutralization, reduces the gastrointestinal crossing of the bacterial toxin from the intestinal surface into central body compartments. Although denaturation processes and a partial proteolytic degradation of the bovine protein molecules take place in the gastrointestinal tract, at least 20% of the ingested amount of the bovine IgG reach the ileocecal valve in presumably active form (N. ROOS et al.: 15N-Labeled Immunoglobulins from Bovine Colostrum Are Partially Resistant to Digestion in Human Intestine. The Journal of Nutrition, 1995, pp. 1238-1244; R. Lissner et al.: Antibody reactivity and fecal recovery of bovine immunoglobulins following oral administration of a colostrum concentrate from cows (Lactobin) to healthy volunteers. International Journal of Clinical Pharmacology and Therapeutics, Vol. 36, No. 5—1998 (239-245)).

Furthermore, various epidemiological studies have yielded indications of a correlation between the size of the calcitriol plasma level of patients and the incidence thereof for various cancers (Stubbins R E et al. 2012. Using components of the vitamin D pathway to prevent and treat cancer. Nutrition Reviews 70: 721-729; Manson J E. 2011. Vitamin D and Prevention of Cancer—Ready for Prime Time?. NEJM 364(15): 1385-87; Pietschmann P. et al. 2003. Bedeutung von Vitamin D im Immunsystem [Significance of vitamin D in the immune system]. J Mineral Stoffwechs 10(3): 13-15; BMJ Research. Association between prediagnostic circulating vitamin D concentration and risk of colorectal cancer in European populations: a nested case-control study BMI/OnlineFirst/bmj.com).

Past investigations indicate an influence of vitamin D receptor-mediated intracellular mechanisms on the crucial deregulated Wnt/β-catenin signaling pathways in tumor cells. Furthermore, vitamin D3 appears, as a result of cooperation with other regulatory signaling pathaways via the human vitamin D receptor as a crucial nuclear receptor in the (tumor) cell, to develop immunoregulatory and anti-tumorigenic effects and also antimicrobial and detoxifying effects (Haussler M R et al. Vitamin D receptor: molecular signaling and actions of nutritional ligands in disease prevention. Nutritional Reviews 2008; 66: 98-112).

In addition, it has recently become clear that there is a distinctly lowered vitamin D receptor density in tumor cells. The reasons for this continue to remain very largely unknown; however, they make therapeutic strategies for elevating the vitamin D level and its receptor density on tumor cells all the more significant.

From the patent literature, some documents describing the use of colostrum or a colostrum preparation—or individual biologically active consitituents therefrom—are known.

For example, EP 0917467 A1 describes the treatment of inflammatory intestinal diseases using colostrum. A reference to the addition of further active ingredients as combination therapy or the treatment of specific diseases cannot be found in the document.

EP 2121002 A1 describes, inter alia, the use of lactoferrin or lactoferrin/metal ions—specifically as a result of later treatment to give 100% iron-saturated lactoferrin—and also at least one antitumor foodstuff factor such as, for example, soy protein for the treatment of cancer. The use of the colostrum or a colostrum preparation—having all the biologically active constituents—without the necessary iron saturation and also the addition of further active ingredients as combination therapy is not described.

SUMMARY OF THE INVENTION

It is an object of the invention to provide a pharmaceutical composition which allows a treatment of diseases in which LPS and/or apoptosis regulation is disturbed.

Furthermore, it is an object of the invention to provide the pharmaceutical composition for use for the treatment of diseases in which LPS and/or apoptosis regulation is disturbed.

This object is achieved by the inventions having the features of the independent claims. Advantageous developments of the inventions are characterized in the dependent claims. The wording of all the claims is hereby incorporated by reference into this description. The inventions also encompass all meaningful and especially all mentioned combinations of independent and/or dependent claims.

Individual method steps will be described in detail below. The steps do not necessarily have to be carried out in the specified order, and the method to be outlined can also comprise further steps that are not mentioned.

It was found that, surprisingly, a pharmaceutical composition containing colostrum or a colostrum preparation and vitamin D can be employed for the prophylaxis and/or for the treatment of diseases in which LPS and/or apoptosis regulation is disturbed.

According to more recent literature references, only vitamins A, B12 and E in low concentrations occur in crude colostrum, for example crude colostrum of bovine origin (A. M. Keech: Peptide Immunotherapy—Colostrum—A Physician's Reference Guide. AKS Publishing 2010). Furthermore, it can be assumed that the fat-soluble vitamins (A, D, E, K), at least in the manufacturing process of all colostrum concentrates, are concomitantly removed in the course of the removal of lipoprotein. They may be present in traces in the end product (A M Keech. Peptide Immunotherapy. Colostrum—A Physician's Reference Guide. AKS Publishing 2010, p. 84). Therefore, in the case of the pharmaceutical composition according to the invention, the vitamin D or vitamin D3 possibly naturally present in the colostrum is certainly not sufficient for developing the desired immunoregulatory action. It must therefore be added to the pharmaceutical composition.

The situation is different for lactoferrin or lactotransferrin. This is a naturally occurring ingredient of colostrum and is, according to the invention, present therein in amounts sufficient for developing the desired pharmaceutical action—together with the further ingredients naturally occurring in colostrum and with the (added) vitamin D3. Therefore, lactoferrin or lactotransferrin is not added to the pharmaceutical composition according to the invention.

Through the specific and novel combination of individual active ingredients known from human and veterinary medicine, it was possible to show according to the invention that the neutralization of lipopolysaccharides (LPS) in the gastrointestinal tract of mammals and the reduction in the LPS-triggered and chronically maintained subclinical inflammation describes a central role for the pathophysiology of septic states, of chronically recurring pain syndrome, and especially for oncogenesis.

Completely unexpectedly, it was possible to show the detection of an increase in action through the use of a combination of individual active ingredients (components). This detected synergism showed a normalization of the most important components of the LPS-triggered inflammation cascade. Especially the restitution of the suppressed apoptosis capacity in peripheral venous monocytes and of the inflammatory cells in the examined, intraoperatively removed tumor tissue of patients with CRC represents an antineoplastic key effect, especially around the time of surgery (i.e., perioperatively) in the treatment of tumor patients (one of the four main types for the therapy of tumor or cancer patients, in addition to radiation therapy, chemotherapy, and targeted therapy using monoclonal antibodies) and also during the chemotherapeutic phases.

In view of the fact that one of the active ingredients used, namely vitamin D3, fundamentally develops its actions through the activation of specific receptors, it was possible to show that the combination of the active ingredients is capable of triggering a qualitatively different immune response insofar as disturbed apoptosis processes in particular in immune cells of CRC patients (more particularly peripheral venous monocytes and those which infiltrate tumor tissue on a large scale) can be revitalized ex vivo and normalized by incubation with the presently used active ingredients and the combination thereof.

In a preferred embodiment of the pharmaceutical composition, said composition is characterized in that the vitamin D present therein is present as vitamin D3 (prohormone: cholecalciferol) and/or as its biologically active form calcitriol, preferably as cholecalciferol.

In a further preferred embodiment of the pharmaceutical composition, said composition is notable for the fact that the vitamin D present therein, preferably vitamin D3 as cholecalciferol and/or as calcitriol, makes up 0.00001-0.5% by weight of the pharmaceutical composition. Preference is given to a content of from 0.00002 to 0.4% by weight, and particular preference is given to a content of between 0.00002 to 0.3% by weight. Very particular preference is given to a content of between 0.00001% by weight and 0.001% by weight or 0.1 µg/g and 10 µg/g, more particularly between 0.00001% by weight and 0.0005% by weight or 0.1 µg/g and 5 µg/g, more particularly between 0.00001% by weight and 0.001% by weight or 0.1 µg/g and 1 µg/g. A content between 0.4 µg/g and 0.6 µg/g is considered to be particularly preferred.

In a further preferred embodiment of the invention, the pharmaceutical composition is notable for the fact that the colostrum comes from mammals selected from the group of the solidungulates (*Equus*; for example horses) or even-toed ungulates (*Artiodactyla* or *Paraxonia*; for example cattle, pigs, camels, goats, sheep). Preferably, the pharmaceutical composition is characterized in that the colostrum present therein comes from ruminants (*Ruminantia*; for example cattle, goats, sheep). It is particularly preferred when the colostrum comes from cattle (*Bovini*). In addition, dairy cows generally tend toward an overproduction of colostrum, which is not completely consumed by the newborn calves.

Preferably, the colostrum comes from cattle which are not kept in animal housing. Such animals are less prone to infectious diseases. Furthermore, the colostrum of such cattle, more particularly of Australian or New Zealand cattle, is notable for the fact that it has hitherto not been possible to measure any seasonal-related differences in the content of bioactivators, as has been observed for example in production batches of European cattle, which are frequently kept in animal housing, for example during the winter months.

In a further preferred embodiment of the invention, the colostrum comes from at least 100, preferably at least 200, individual colostra. A colostrum obtained from many individual colostra exhibits many advantages over colostrum obtained from few individual colostra. For example, it is polyvalent, i.e., it exhibits a high level of homogeneity and the concentration of the active ingredients and the activities thereof are batch-independent. It can be manufactured in accordance with the EU GMP guidelines (guidelines for quality assurance in production, equipment, media and cleanroom environment in the production of medicaments and active ingredients, cosmetics, foodstuffs and feedstuffs). Hyperimmune concentrates, however, are preparations which are obtained from few individual colostra, frequently from vaccinated mothers (e.g., cows), and which are used in patients suffering from infectious diseases determined by differential diagnosis. Preferably, the colostrum according to the invention has been produced and delivered within the first 24 hours to 72 hours after birth, particularly preferably within the first 48 hours, more particularly within the first 24 hours, after birth. It is of great importance that the colostrum is received within these periods, since the content of cytokines in the colostrum can change greatly after birth.

Fundamentally, the pharmaceutical composition according to the invention can be present in all administration forms which are pharmaceutically meaningful and known to a person skilled in the art, for example as powder, tablets, capsules, spray, liquid or suppositories. It can be present in pure form, but also as concentrate, for example as powder concentrate, of a particularly preferred embodiment of the invention. Furthermore, it can additionally contain all filling materials and additives, for example fillers, binders, disintegrants and glidants, which are required for use as pharmaceutical composition and in accordance with the selected application form or administration form (e.g., endobronchial, enteral, epidural, inhalational, intra-arterial, intra-articular, intragastric, intracardiac, intracutaneous, intralumbar, intralymphatic, intramammary, intramuscular, intraneural, intraperitoneal, intrapleural, intrapulmonary, intratracheal, intraurethral, intrathecal, intravenous, intranasal, oral (also locally effective therein when it, for example, is kept in the oral cavity for a few minutes and is then thereby gargled. This has so far been proven in the case of initial signs of tonsillitis, pharyngitis, laryngitis. In the prodromal stage of viral flu, there was an immediate elimination of subjective symptoms for patients, such as fever, pain in the limbs/back pain or fatigue), peroral, parenteral, percutaneous, peridural, perineural, rectal, sublingual, subconjunctival, subcutaneous, systemic, topical, transdermal, vaginal) and are known to a person skilled in the art and be present, for example, even in a lyophilized state.

In a preferred embodiment, the colostra are defatted, filtered and pasteurized (e.g., at 72° C. for 15 s) before a powder is manufactured by drying, preferably spray drying.

In a further preferred embodiment of the invention, the colostrum of the pharmaceutical composition, preferably when said colostrum is present as powder concentrate, comprises 70-90% by weight of protein and less than 5% by weight of fat.

In a further preferred embodiment, the colostrum of the pharmaceutical composition comprises 70-90% by weight of protein, less than 5% by weight of fat and less than 0.2 µg/100 g vitamin D.

In a further preferred embodiment, the colostrum of the pharmaceutical composition comprises 75-90% by weight of protein, less than 2% by weight of fat and less than 0.2 µg/100 g vitamin D.

Instead of less than 2% by weight, the content of fat can also be between 0.5 and 2% by weight.

In a further preferred embodiment, the protein share of the abovementioned colostra contains with preference over 20% by weight of IgG (measured by HPLC), preferably 20-30% by weight, particularly preferably between 20 and 24% by weight, preferably IgG of the IgG1 subclass, and 1-5% by weight of lactoferrin or lactotransferrin, based on the total weight of the colostrum.

A particularly preferred composition of the colostrum powder in the pharmaceutical composition is shown by Table 2.

In a preferred embodiment of the invention, the recommended daily dose of the pharmaceutical composition is between 5 and 50 g, preferably between 5 and 15 g.

In a particularly preferred embodiment of the invention, the diseases which are to be treated and/or which are to be controlled prophylactically using the pharmaceutical composition and in which LPS and/or apoptosis regulation is disturbed are malignant diseases, more particularly tumor diseases (cancer), preferably tumors of the gastrointestinal tract such as, for example, intestinal cancer, stomach cancer, pancreatic cancer, particularly preferably colorectal cancers (CRC). Intestinal cancer is understood according to the invention to mean all malignant tumors of the intestine, especially including colorectal cancers (CRC), which make up more than 95% of malignant intestinal tumors.

In Germany, intestinal cancer is, for men and women, the second most common cancer (besides breast cancer), which more than 6% of all Germans develop over their lifetime. Colorectal cancers initially very rarely cause symptoms; they almost always develop from initially benign intestinal polyps. The chances of being cured by means of surgery and chemotherapy with a 5-year survival rate of from 40 to 60% on average depends crucially on the disease stage in which the intestinal cancer is discovered.

The pharmaceutical composition according to the invention can, as indicated several times, be employed not only for treating diseases which have specifically occurred and which are associated with LPS and/or apoptosis regulation being disturbed; on the contrary, said composition can also be used for prophylaxis against the occurrence of said diseases. For example, a colostrum or a preparation based thereon and vitamin D3 could be provided in amounts suitable for regular consumption, and so said composition can be ingested prophylactically and thus help to reduce the probability of the occurrence of the disease.

In a further preferred embodiment, the pharmaceutical composition according to the invention is used for the prophylaxis and/or for the treatment of diseases in which LPS and/or apoptosis regulation is disturbed. Particularly preferably, the diseases are malignant diseases, more particularly tumor diseases (cancer), preferably tumors of the gastrointestinal tract such as, for example, intestinal cancer, stomach cancer, pancreatic cancer, particularly preferably colorectal cancers (CRC).

In a particularly preferred embodiment, the diseases are colorectal cancers (CRC) of UICC stages I to IV, preferably of UICC stages I to III, very particularly preferably of UICC stages I to II.

In this connection, treatment in the case of malignant diseases can also be understood to mean the reduction of adverse effects of a further therapy, for example a chemotherapy. This also includes the reduction of the perioperatively elevated risk of a tumor metastasis.

Further details and features are revealed by the following description of preferred exemplary embodiments in conjunction with the dependent claims. Here, the particular features can be realized on their own or as two or more features in combination with one another. The possibilities of achieving the object are not restricted to the exemplary embodiments. For example, specified ranges always encompass all—unmentioned—intermediate values and all conceivable subintervals.

The exemplary embodiments are depicted schematically in the figures. The same reference numerals in the individual figures refer to elements which are the same or functionally identical or correspond to one another in terms of their functions. Specifically:

DETAILED DESCRIPTION OF THE INVENTION

Figure 1A:
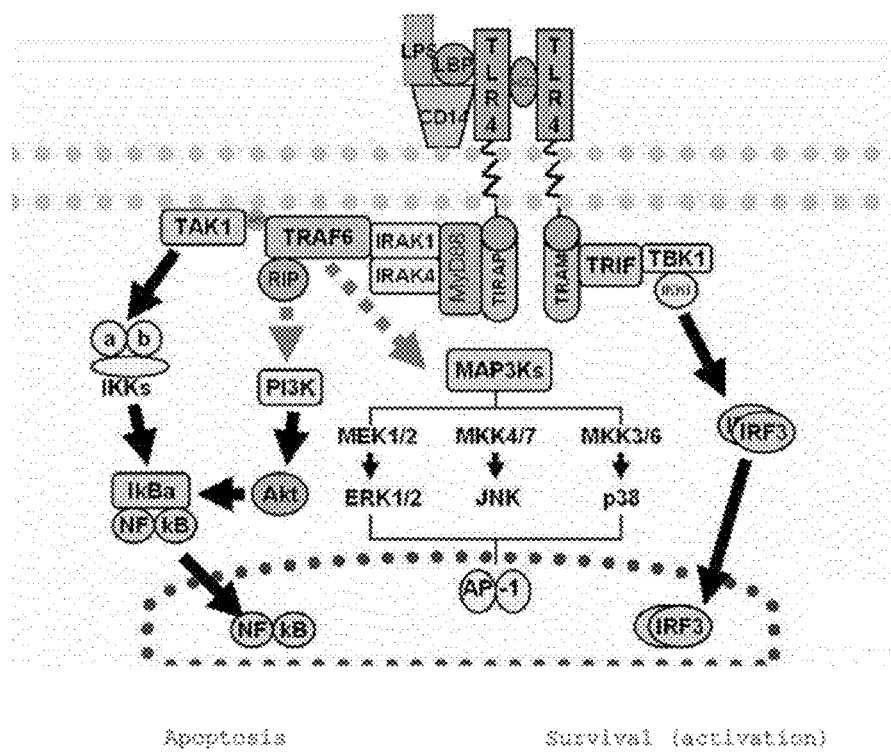
FIGS. 1a,b show a schematic diagram of the TLR4 signaling pathway as a representative target structure of the pharmaceutical composition according to the invention
Figure 1B:
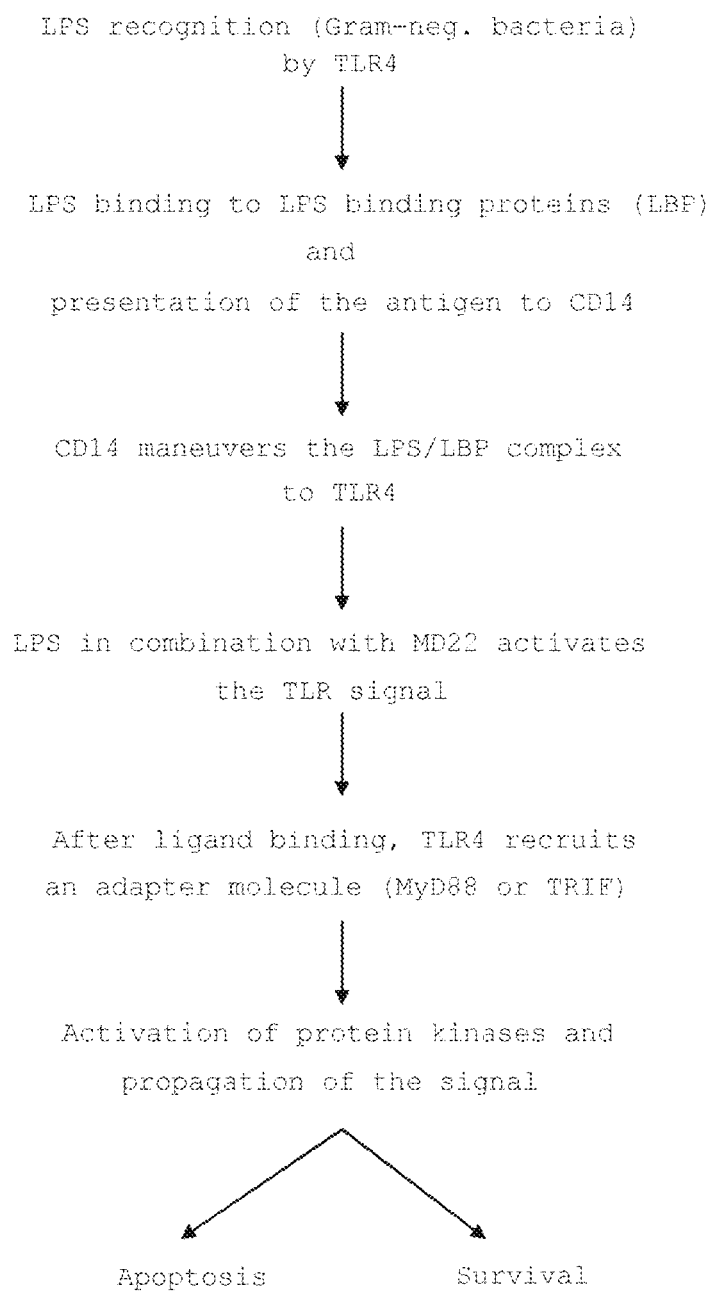

FIGS. 1 a, b show typical cellular reaction patterns which are elicited in the course of an inflammation response which is forming. A crucial role is played here especially by the reactivity of the immune system of a patient with respect to LPS, which comes from the break-up of Gram-negative pathogens (e.g., *Escherichia coli* and Enterococci) in blood and on mucosal surfaces. This is depicted in part in FIG. 1. The order of events is depicted in FIG. 1b in a flow chart.

Figure 2:
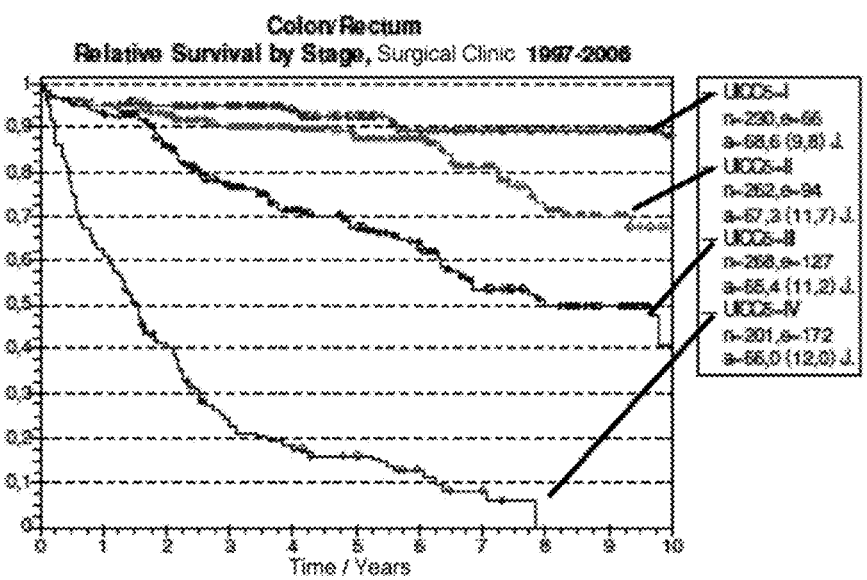
FIG. 2 shows a graphical representation of the overall survival rates of the long-term follow-up of different intestinal cancer patients (colon cancer tumor development); CRC overall survival interim analysis, Comprehensive Cancer Center UKW Würzburg, 1997-2006, n=961 patients; the table shows the classification of the individual UICC stages according to the TNM system.

FIG. 2 shows a graphical representation of the overall survival rates of the long-term follow-up of different intestinal cancer patients (colon cancer tumor development; TNM system: Union International Contre le Cancer, UICC stage I-IV).

Figure 3:
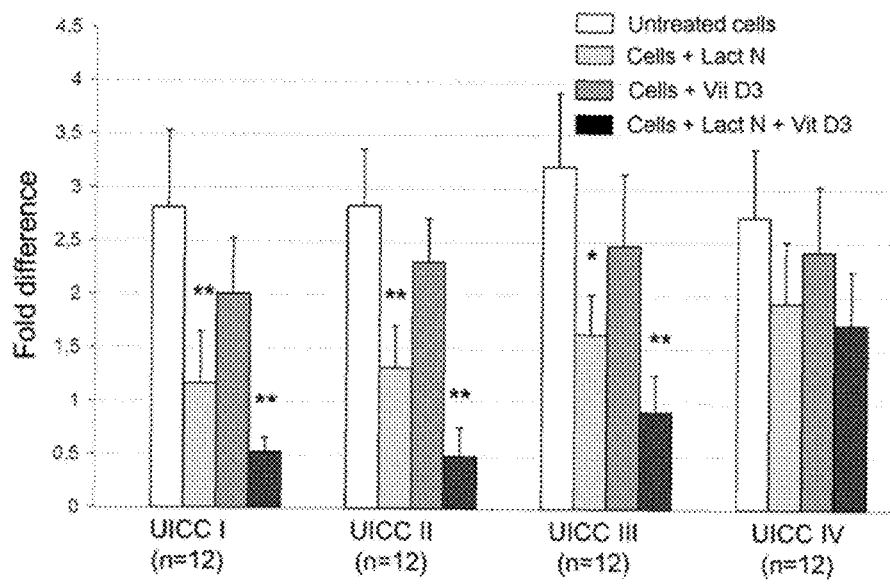
FIG. 3 shows a bar chart of the measured expression of the CD68 gene in monocytes from the blood of patients with CRC of UICC stages I to IV (measurement by RT-qPCR); * p<0.001; ** p<0.0001 in comparison with untreated cells; 12 samples in each case for each UICC stage (bars from left to right for each stage: untreated cells, cells+Lactobin N, cells+vitamin D3, cells+Lactobin N+vitamin D3)

FIG. 3 shows a lowered expression of the CD68 gene in MNC from CRC patients with incubation with the colostrum preparation Lactobin® N. Furthermore, it is possible to show an additional synergistic effect in the coincubation of Lactobin® N and vitamin D3.

Figure 4:
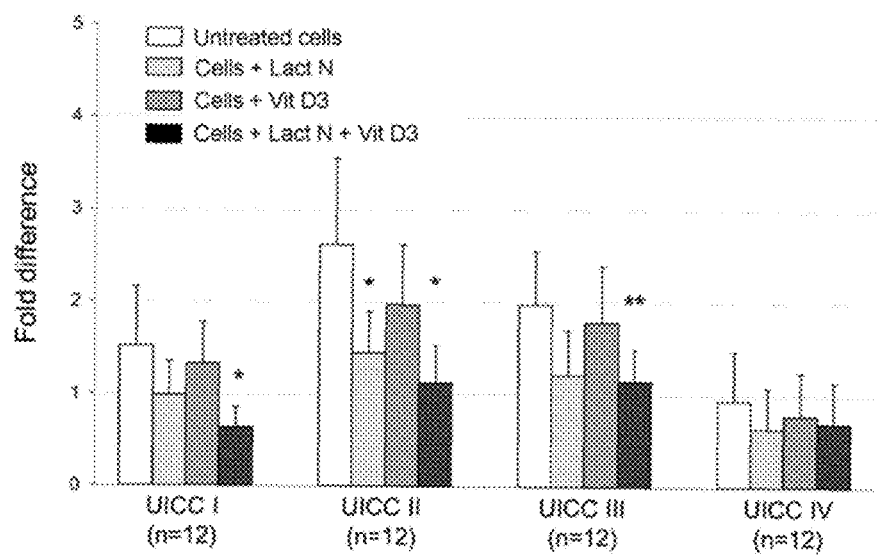
FIG. 4 shows a bar chart of the measured expression of the TLR4 gene in monocytes from the blood of patients with CRC of UICC stages I to IV (measurement by RT-qPCR); * p<0.001; ** p<0.01 in comparison with untreated cells (bars from left to right for each stage: untreated cells, cells+Lactobin N, cells+vitamin D3, cells+Lactobin N+vitamin D3)

FIG. 4 shows a lowered expression of the TLR4 gene in MNC from CRC patients with incubation with Lactobin® N.

Figure 5:
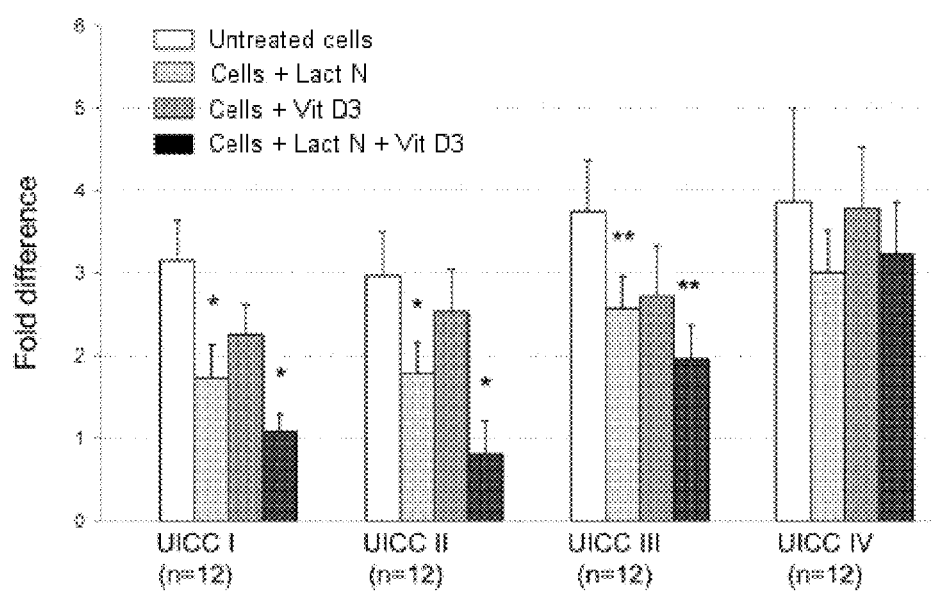
FIG. 5 shows a bar chart of the measured expression of the IGF 1 gene in monocytes from the blood of patients with CRC of UICC stages I to IV (measurement by RT-qPCR); * p<0.001; ** p=0.02 in comparison with untreated cells (bars from left to right for each stage: untreated cells, cells+Lactobin N, cells+vitamin D3, cells+Lactobin N+vitamin D3)

FIG. 5 shows a lowered expression of the IGF-1 gene in MNC from CRC patients with incubation with Lactobin® N. It is possible to show an additional synergistic effect in patients of UICC classes I-III in the case of coincubation of Lactobin® N and vitamin D3.

FIG. 5 shows an elevated apoptosis rate of CD68-positive MNC in CRC patients with incubation with Lactobin® N. Furthermore, it is possible to show an additional synergistic effect in the case of coincubation of Lactobin® N with vitamin D3 (representative example, UICC II).

Figure 7:
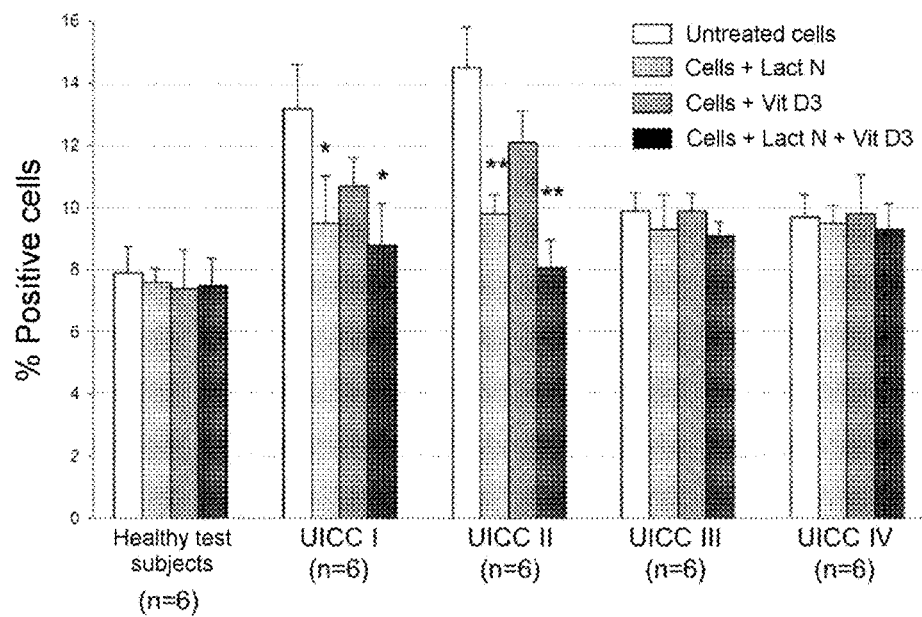
FIG. 7 shows a bar chart of the measured monocyte counts in the peripheral blood count of patients with CRC of UICC stages I to IV (FACS analysis); * p<0.001; ** p<0.0001 in comparison with untreated cells (bars from left to right for each stage: untreated cells, cells+Lactobin N, cells+vitamin D3, cells+Lactobin N+vitamin D3)

FIG. 7 shows a lowered monocyte count in the peripheral blood count of CRC patients with incubation with Lactobin® and also an additional synergistic effect in UICC I and II patients in the case of coincubation of Lactobin® N and vitamin D3.

Figure 8:
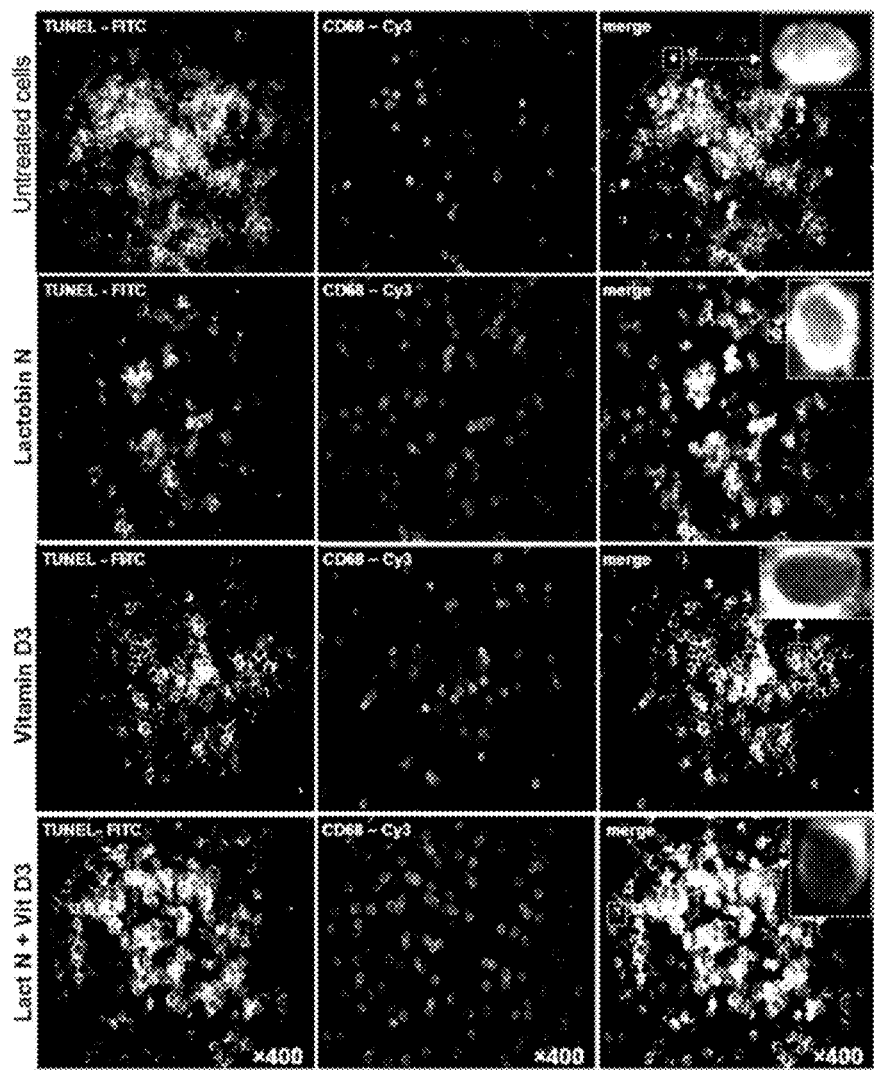
FIG. 8 shows Tunel stainings of CD68-positive macrophages (CD68) from tumor cells of CRC patients (representative example for UICC II)

FIG. 8 shows an elevated apoptosis rate of CD68-positive macrophages from tumor cells in CRC patients with incubation with Lactobin® N. Furthermore, it is possible to show an additional synergistic effect in the case of coincubation of Lactobin® N with vitamin D3 (representative example, UICC II).

Figure 9:
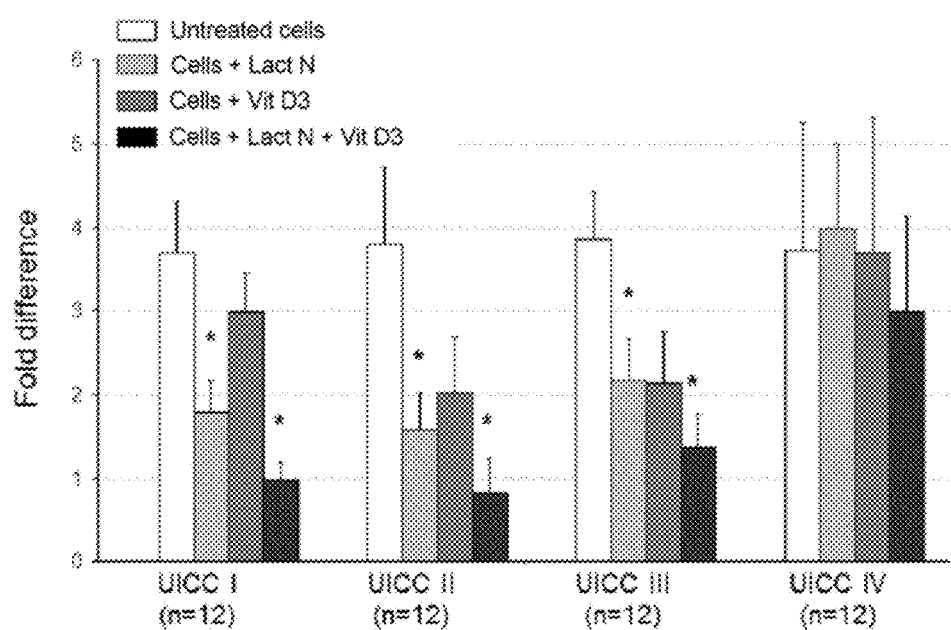
FIG. 9 shows a bar chart of the measured expression of the CD68 gene in the tumor compartment of patients with CRC of UICC stages I to IV (measurement by RT-qPCR); * p<0.0001 in comparison with untreated cells (bars from left to right for each stage: untreated cells, cells+Lactobin N, cells+vitamin D3, cells+Lactobin N+vitamin D3)

FIG. 9 shows a lowered expression of the CD68 gene in the tumor compartment of CRC patients with incubation with the colostrum preparation Lactobin® N. Furthermore, it is possible to show an additional synergistic effect in the coincubation of Lactobin® N and vitamin D3.

Figure 10:
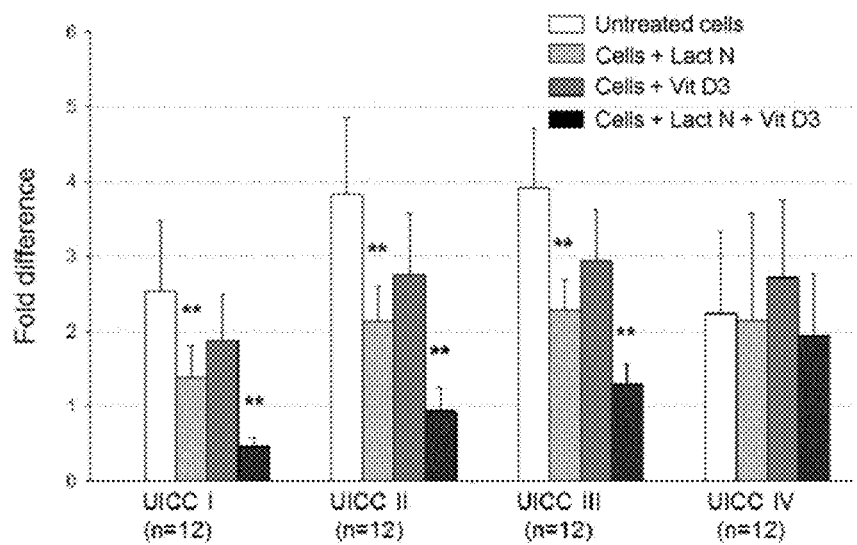
FIG. 10 shows a bar chart of the measured expression of the CD14 gene in the tumor compartment of patients with CRC of UICC stages I to IV (measurement by RT-qPCR); * p<0.0001 in comparison with untreated cells (bars from left to right for each stage: untreated cells, cells+Lactobin N, cells+vitamin D3, cells+Lactobin N+vitamin D3)

FIG. 10 shows a lowered expression of the CD14 gene in the tumor compartment of CRC patients with incubation with the colostrum preparation Lactobin® N. Furthermore, it is possible to show an additional synergistic effect in the coincubation of Lactobin® N and vitamin D3 for UICC I to UICC III patients.

Figure 11:
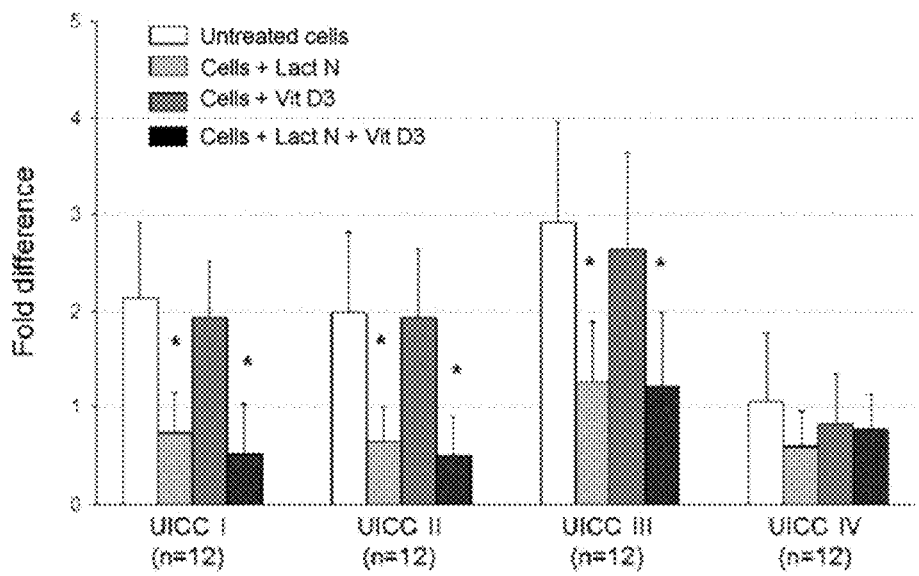
FIG. 11 shows a bar chart of the measured expression of the TLR4 gene in the tumor compartment of patients with CRC of UICC stages I to IV (measurement by RT-qPCR); * p<0.001 in comparison with untreated cells (bars from left to right for each stage: untreated cells, cells+Lactobin N, cells+vitamin D3, cells+Lactobin N+vitamin D3)

FIG. 11 shows a lowered expression of the TLR4 gene in the tumor compartment of CRC patients with incubation with the colostrum preparation Lactobin® and also in the coincubation of Lactobin® N and vitamin D3.

Figure 12:
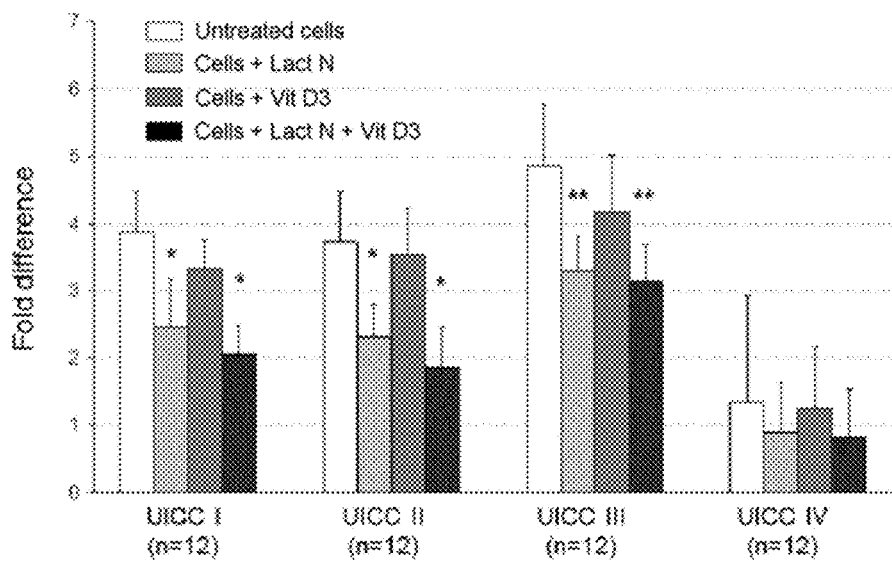
FIG. 12 shows a bar chart of the measured expression of the IGF 1 gene in the tumor compartment of patients with CRC of UICC stages I to IV (measurement by RT-qPCR); * p<0.001; ** p<0.01 in comparison with untreated cells (bars from left to right for each stage: untreated cells, cells+Lactobin N, cells+vitamin D3, cells+Lactobin N+vitamin D3)

FIG. 12 shows a lowered expression of the IGF1 gene in the tumor compartment of CRC patients with incubation with the colostrum preparation Lactobin® N. Furthermore, it is possible to show an additional synergistic effect in the coincubation of Lactobin® N and vitamin D3.

Figure 13:
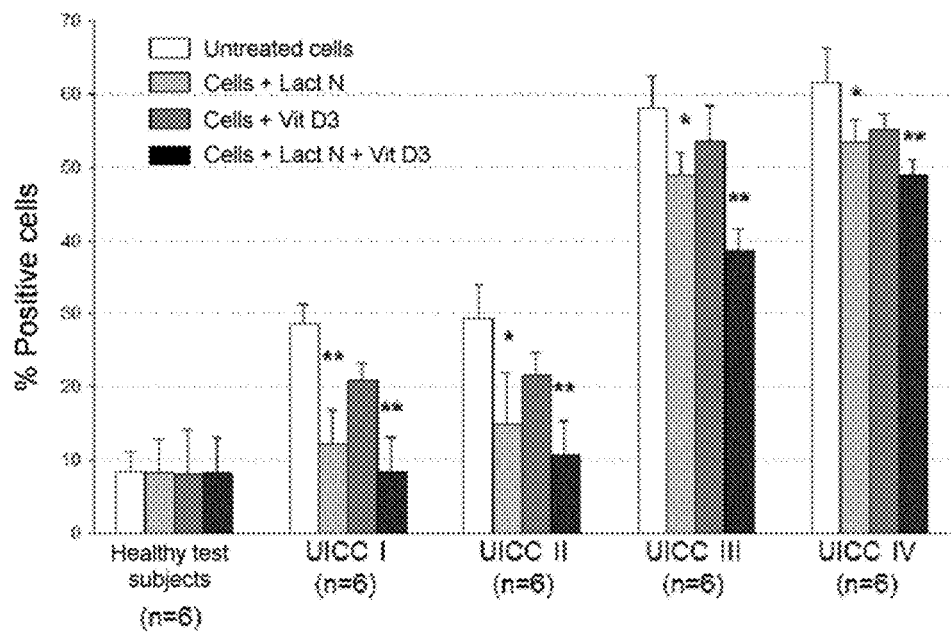
FIG. 13 shows a bar chart of the measured CD14 expression in MNC of patients with CRC of UICC stages I to IV (FACS analysis); * p<0.001; ** p<0.0001 in comparison with untreated cells (bars from left to right for each stage: untreated cells, cells+Lactobin N, cells+vitamin D3, cells+Lactobin N+vitamin D3)

FIG. 13 shows a lowered expression of the CD14 gene in MNC of CRC patients with incubation with the colostrum preparation Lactobin® N. Furthermore, it is possible to show an additional synergistic effect in the coincubation of Lactobin® N and vitamin D3.

Figure 14:
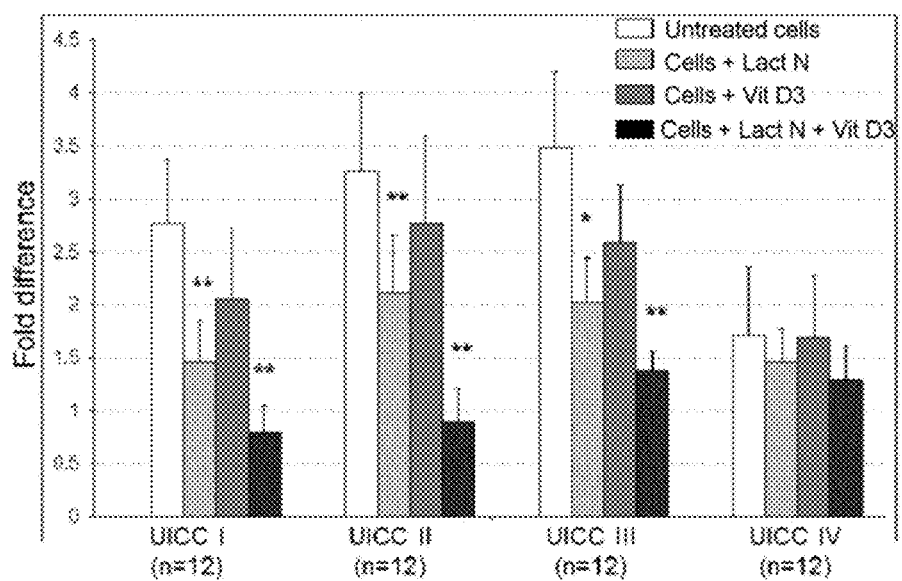
FIG. 14 shows a bar chart of the measured expression of the CD14 gene in MNC of patients with CRC of UICC stages I to IV (measurement by RT-qPCR); * p<0.001; ** p<0.0001 in comparison with untreated cells (bars from left to right for each stage: untreated cells, cells+Lactobin N, cells+vitamin D3, cells+Lactobin N+vitamin D3)

FIG. 14 likewise shows a lowered expression of the CD14 gene in MNC of CRC patients with incubation with the colostrum preparation Lactobin® N. Furthermore, it is possible to show an additional synergistic effect in the coincubation of Lactobin® N and vitamin D3.

Figure 15:
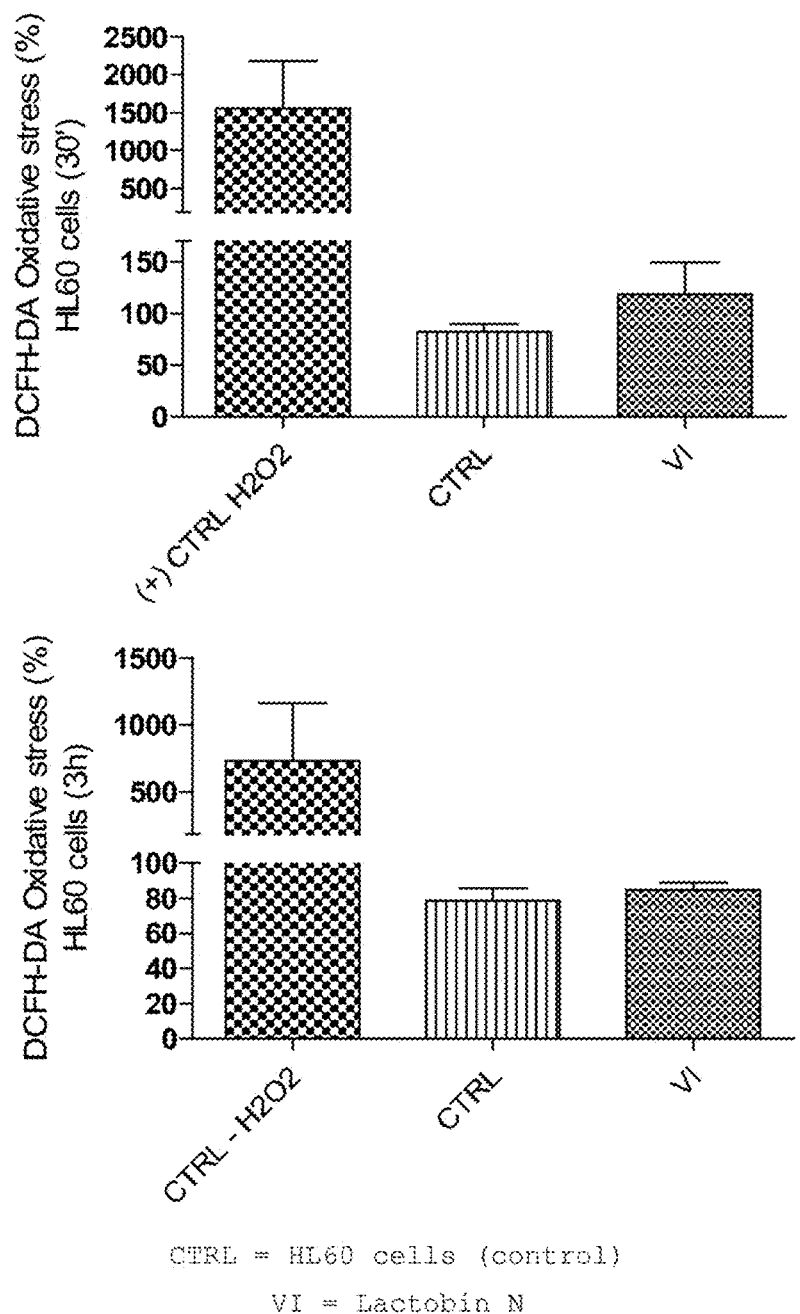
FIG. 15 shows a bar graph of the measured values of the DCFH-DA (dichlorodihydrofluorescein diacetate) assay in HL60 cells (human promyelocytic leukemia cells) (top: 30 min, bottom: 3 h)

FIG. 15 shows no significantly altered oxidative stress in HL-60 cells after incubation with Lactobin®. Neither after a 30-minute incubation nor after a 3-hour incubation was there a significant increase in the oxidative stress.

Figure 16:
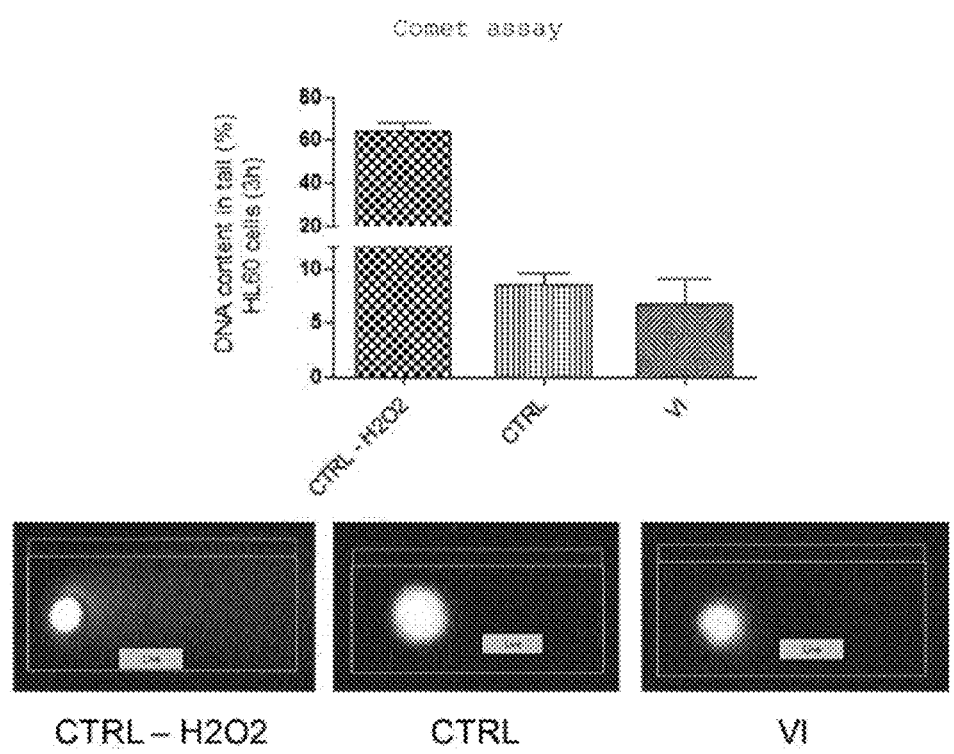
FIG. 16 shows a bar graph of the measured values of the comet assay in HL60 cells (3 h) and a graphical representation of the assay.

FIG. 16 shows the so-called comet assay (also called single-cell gel electrophoresis), a gel electrophoresis technique which makes it possible to determine DNA damage in single cells. Using said assay, it is possible to detect DNA single-strand and double-strand breaks. The principle behind the comet assay is based on cells embedded in agarose being lysed and exposed to an electric field (electrophoresis). During electrophoresis, the negatively charged DNA migrates to the positive terminal and, owing to the pores in the agarose, the fragments are resolved according to size, since the smaller fragments cover a further distance within a certain time than the larger ones. However, chromosomal DNA is too large for migrating as a whole in the electric field. Only damaged, fragmentary DNA is capable here of migrating out of the cell nucleus. Under a UV microscope, the damaged cells, which have previously been stained with fluorescent dyes such as ethidium bromide, then appear with a tail of DNA fragments, which gives them the appearance of a comet. For the comet assay, it is possible to use all cells which have a cell nucleus. What is evaluated is the number of damaged and undamaged cell nuclei. In said assay, it was not possible to observe any significant change in DNA damage in HL-60 cells after a three-hour incubation with Lactobin® N.

Figure 17:
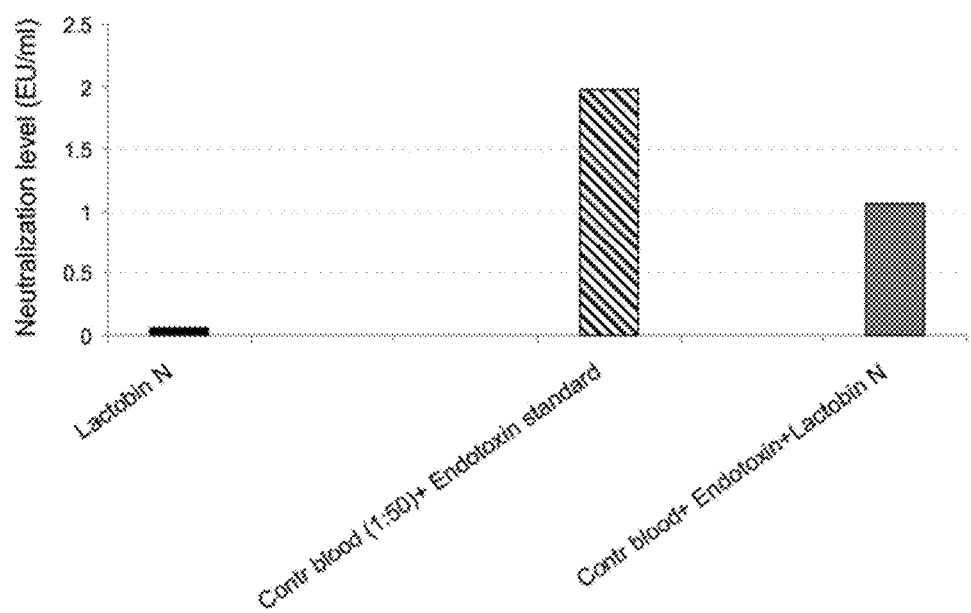
FIG. 17 shows a bar graph of the measured background endotoxin levels in Lactobin N and also the neutralization capacity of the Lactobin N.

FIG. 17 shows negligible endotoxin levels in Lactobin N (black bar). Furthermore, the figure shows the neutralization capacity of Lactobin N. Compared with endotoxin on its own as control, a distinct neutralization (approx. 50%) is shown with the addition of Lactobin N.

Figure 18:
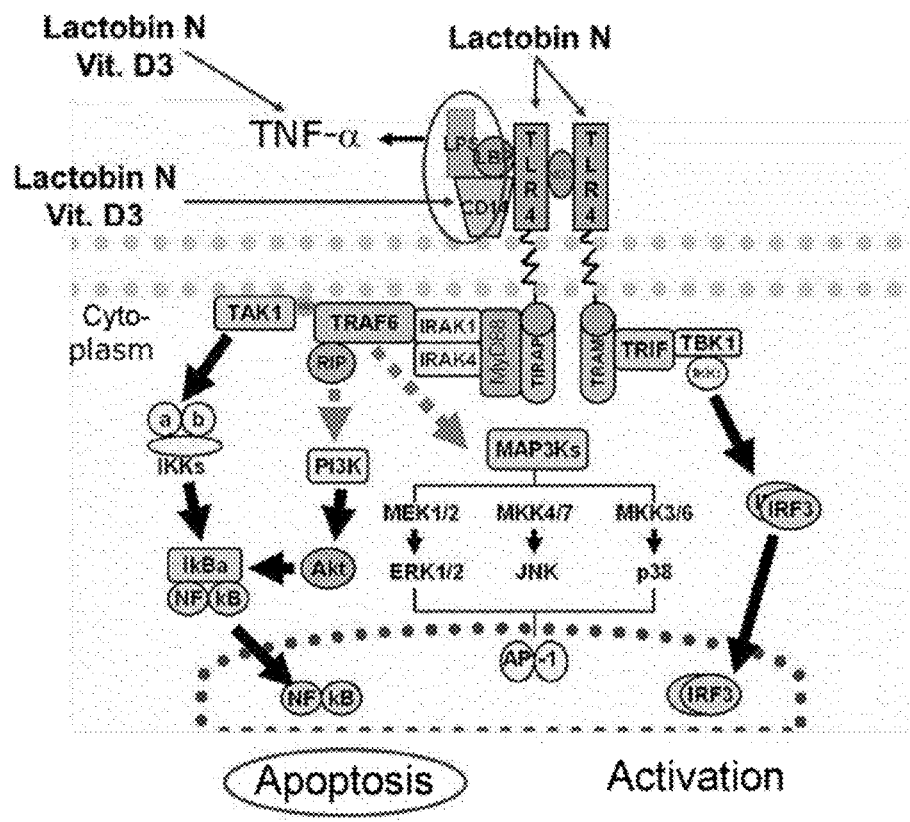
FIG. 18 shows a schematic diagram of typical cellular reaction patterns in the course of an inflammation response which is forming and mechanism of action of the pharmaceutical composition according to the invention.

FIG. 18 shows typical cellular reaction patterns elicited in the course of an inflammation response which is forming and also the mechanism of action of the composition according to the invention.

It is possible to realize numerous variations and developments of the described exemplary embodiments.

Material and Methods

The examined tumor tissue and the peripheral blood come from patients with diagnosed intestinal cancer (colorectal carcinoma; CRC), which were stored frozen in the tumor tissue, cell and sera bank of Universität Würzburg, Chirurgische Klinik and Poliklinik, Zentrum für Operative Medizin [University of Würzburg, surgical clinic and polyclinic, center for operative medicine]. Mononuclear cells from whole blood and intraoperatively removed tumor tissue provided the experimental results.

Peripheral blood mononuclear cells (PBMC, i.e., mononuclear cells (MNC)). This refers to mononuclear blood cells which have a round cell nucleus. These are, for example, lymphocytes and monocytes. Said cells play an important role in the immune system in controlling infections. PBMC or MNC are frequently employed in diagnostics as an indicator for infections which are present, as a factor for prognosing the course of an HIV infection and in clinical research. From the blood and sera collection of the tumor tissue bank and the tumor cells of an individual tumor patient that were likewise stored in said bank, they were, after passing through a specific thawing/revitalization procedure, examined for their protein and gene expression, apoptosis behavior and their released messenger substances (cytokine profiles) under the influence of the colostrum preparation Lactobin® N, vitamin D3 and also the combination in a specifically selected repertoire of methods.

Isolation of Serum and Mononuclear Cells from the Patient Blood

After collection, EDTA tubes were left to stand at room temperature (RT) for 60 min. Thereafter, serum was removed, divided into portions (1 ml/tube) and stored in −80° C. The blood was centrifuged at 311 g for 10 min. Thereafter, 1 part whole blood+5 parts lysis buffer were mixed, left to stand at RT for 15 min and then centrifuged at 311 g for 10 min. The supernatant was discarded and the pellet was washed with RPMI 1640 medium (repeated 3×). The cells were then counted and frozen at −170° C. in nitrogen at $5 \times 10^6$/ml (freezing medium: RPMI 1640 medium containing 5% DMSO, dimethyl sulfoxide=cryopreservation). In addition, the immune status was measured from one tube (FACS analysis, see below).

Isolation of Tumor Cells from the Colon Carcinoma Preparations

From each patient, a sample of the colon carcinoma and of the normal tissue (of the tumor-bearing colon) was removed on the oral side (proximally, in the direction of the upper gastrointestinal tract) and saved for examinations according to the following scheme: for the molecular biology analysis and immunohistological examination, the preparations were stored in freezing tubes and Tissue Tek tubes in liquid nitrogen at −194° C. until they were processed; for the extraction of RNA, tissue samples were stored at 4° C. overnight with approx. 1.7 ml of RNA stabilizer and later frozen in liquid nitrogen at −194° C.; for the analysis of tumor cells, tumor cell suspensions were prepared by means of collagenase treatment and a cell strainer and cryopreserved.

Thawing Procedure

The cryotube to be thawed was removed from the nitrogen and immediately transferred to a 37° C. water bath. Once the cells had detached from the inner wall of the cryotube (1-1.5 min), they were transferred to a sterile 50 ml Falcon tube containing 40 ml of cold medium. After a 5-minute centrifugation at 400 g, the medium was removed, the cell pellet was resuspended in 6 ml of warmed-up medium and the cells were counted.

Flow Cytometry (FACS Analysis)

Peripheral blood cells (MNCs, $5\times10^5$) were stained with PE-conjugated anti-CD14, FITC-conjugated anti-CD45 and 7 AAD, PE-conjugated anti-CD25, FITC-conjugated anti-CD3 and 7 AAD and PE-conjugated anti-mouse IgG2a. All the antibodies were purchased from Beckman Coulter (Krefeld, Germany). Four-color flow cytometry was carried out on a FACS-Epics XL-MCL (Beckman Coulter) and the cells were analyzed using the Expo 32 acquisition software (Beckman Coulter). Viable lymphocytes were selected by gating and $10^5$ events were recorded.

Protein Analysis to Determine IGF-1

The examinations were carried out in order to detect the cytokine insulin-like growth factor 1 (IGF-1) present in the samples. To this end, use was made of enzyme-linked immunosorbent assay (ELISA) sets (from Biosource International, California, USA) in accordance with the protocol instructions from the manufacturer. 50 µl of standard sample, control and the samples were pipetted per well into 96-well plates coated with anti-IGF-1. Thereafter, 50 µl of biotin conjugate (second antibody against IGF-1) were added. Subsequently, the plates were incubated at room temperature for 90 min, washed four times, and 100 µl of streptavidin-HRP working solution were pipetted into the wells and the plate was incubated at room temperature for 45 min. Thereafter, the plates were again washed four times, 100 µl of stabilized chromogen were added and incubated at room temperature for 30 min. Lastly, 100 µl of stop solution were pipetted. The results were read off on the ELISA reader at 450 nm (Dynatech Laboratories, Sullyfield, USA).

Protein Analysis to Determine Cytokines (Luminex Analysis)

Serum of whole blood samples was obtained by centrifugation and stored at −80° C. until analysis. Aliquots of the serum were analyzed with blinding of the diagnosis.

Interleukin (IL)-12 and proinflammatory factors such as IL-10, IL-6, IFN-γ, TNF-α and anti-inflammatory factors such as IL-10 and IL-13 in the serum samples were measured in duplicate using an immunobead-based multiplex assay. The assays were carried out on a Bio-Plex system (Biosource).

The microspheres coated with mixtures of corresponding capture antibodies and the labeled detection antibodies were purchased from Biosource (Camarillo, Germany). The reagents had already been tested and qualified by the manufacturer to rule out a cross-reactivity of the antibody-coated microspheres.

The Luminex measurements were carried out in order to determine further expressed MNC cytokines. 25 µl of antibody-coated microspheres were added to 96-well plates [mixture of the cytokines GM-CSF, IFN-γ, IL-1β, IL-2, IL-4, IL-5, IL-6, IL-8, IL-10 and TNF-α; ready-prepared kit, from Biosource International, California, USA]. After washing had been carried out twice, 50 µl of incubation buffer, 50 µl of ready-prepared sample dilution and 50 µl of sample were pipetted into each well. The plates were incubated in the dark on a shaker for 2 hours at room temperature and again washed twice. Thereafter, 100 µl of the biotinylated detection antibody were added to each well, incubated in the dark on a shaker for a further hour at room temperature, and again washed twice. 100 µl of SAV-RPE (R-phycoerythrin fluorescent dye, from Biosource International) were pipetted into each well, the plates were again shaken in the dark for 30 min at room temperature and washed three times. Each assay preparation was adjusted with 100 µl of wash buffer per well as the final volume and the plates were measured in the Luminex reader (Luminex 100, from Luminex Applied Systems, Sheffield, UK).

Cytospins

After thawing, the cell suspension composed of MNCs and tumor cells was washed in RPMI 1640 medium, centrifuged at 311 g for 10 min and adjusted to a cell count of $1\times10^5$ cells per ml. 50 µl of cell suspension were added to each Cytospin chamber and centrifuged for 1 min. The slides were inspected under a microscope and dried at room temperature for 2 hours.

To adhere the cells on slides, they were fixed into a Shandon Cytospin 2 centrifuge [Thermo Shandon, Pittsburgh, USA]. The centrifuge contains 12 positions for fastening the slides. A piece of perforated paper is fitted between the slide and the filling funnel in order to suck off the excess liquid. After thawing (−80° C.), the cells were centrifuged down and washed twice in PBS. Subsequently, 50 µl of the cell suspension containing $2\times10^6$ cells/ml of each sample were filled into the funnels and the slides were centrifuged below 550 g for 1 min. The slides were then air-dried overnight at room temperature. Then, they were processed in accordance with the TUNEL assay protocol.

In Situ Detection of Apoptosis by Means of TUNEL Assay

A non-isotope-based in situ DNA end labeling technique, using digoxigenin-dNTP and a terminal transferase, was used in order to identify cells containing fragmented DNA (ApopTag® Plus Peroxidase In Situ Apoptosis Kit, Chemicon, Planegg, Munich, Germany). Cytospins of peripheral blood lymphocytes were fixed and the endogenous peroxidase was quenched with 0.1% hydrogen peroxide. The cells were equilibrated in the buffer of the terminal transferase before the reaction buffer containing digoxigenin-dNTP oligonucleotide was added. The oligonucleotides extended by the digoxigenin-dNTP were detected using an anti-digoxigenin-peroxidase conjugate, diluted with a blocking agent, followed by staining (Nova Red, Linaris, Wertheim-Bettingen, Germany) and a double-stain block (DAKO, Jena, Germany) to prevent a cross-reaction with the surface staining. The CD68 (monocytes) antibody (DAKO) was incubated overnight in a humidity chamber. After washing, the Cytospins were incubated with an anti-mouse antibody conjugated with an alkaline phosphatase (DAKO). The Cytospins were again washed and stained (VECTOR Black Substrate Kit, Vector Laboratories, Peterborough, UK) and counterstained (hemalaun staining). For the negative controls, the Cytospins were incubated with the TUNEL reaction mixture without the terminal transferase (TdT).

TUNEL/CD68 double staining was carried out in order to identify and count apoptotic CD68 cells in the peripheral blood. First, TUNEL staining was carried out as described above, with Nova Red as substrate. Thereafter, an anti-CD68 antibody (DAKO) was used, followed by the incubation with VECTOR Black as substrate. When the treated samples were observed under a light microscope, the CD68-positive cells are stained black, whereas the double-positive TUNEL/CD68-positive cells exhibit a red staining of the cell nucleus.

The apoptotic index (AI) was defined as the ratio between TUNEL-positive infiltrated cells to all counted infiltrated cells×100. For each group, the number of stained cells at a magnification of 400× in at least 10 high-power fields (400×) were counted. The cells were classified as apoptotic when the entire surface of the cell nucleus was labeled as positive.

Gene Expression Analysis

Extraction of RNA

RNA was extracted from MNCs and homogenized tumor tissue using the RNA Extraction Kit (Qiagen, Hilden, Germany), washed in DEPC 75% ethanol solution and then stored at −70° C. until it was processed further. The amount of RNA was determined by measuring absorption at 260 nm. The 260:280 ratio was determined within the 1.8-2.0 range; it was thus possible to prevent a contamination of the RNA by proteins.

Preparation of cDNA (Reverse Transcription)

Complementary DNA (cDNA) was prepared using the iScriptTMcDNA Synthesis Kit (Bio-Rad, Munich): 12 µl of 5× iScript Reaction Mix and 3 µl of iScript Reverse Transcriptase were added to 45 µl of each solution containing 3 µg of each RNA in nuclease-free distilled $H_2O$. This yielded a volume of 60 µl for each sample. In the iCycler (Bio-Rad, Munich), the reverse transcription of mRNA to cDNA was carried out according to the following transcription protocol: 5 min at 25° C., 30 min at 42° C. and 5 min at 85° C. After completion of the reaction, the temperature was held at 4° C. The cDNA was stored at −20° C.

Quantitative Real Time PCR

The 'real-time reverse transcription polymerase chain reaction' method (real-time RT-PCR for short) is used for determining the expression of various genes. Said method allows the quantification of the expression of a gene in question in relation to the control genes.

The PCR was used to analyze the CD14, CD68, TLR4 and IGF-1 mRNA expressed in the MNC and colon carcinoma samples. The primers were created using the Primer Express Software for primer design in order to produce short amplicons of 100-200 base pairs of the defined cDNA. The quantitative real-time PCR was carried out using 11.5 µl of LightCycler DNA Master SYBR Green I mix (Applied Biosystems, Darmstadt, Germany) with 2 µl of cDNA (50 ng/µl), 0.3 µM forward primer and 0.3 µM reverse primer to give a total reaction volume of 23 µl. The PCR cycle consisted of a 15-minute initial denaturation at 95° C., followed by 40 cycles of 15-second denaturations at 95° C., a 30-second annealing at 55-61° C. and a 3-second extension at 72° C. Gene-specific products were continuously measured using the ABI Prism 7700 sequence detector (Applied Biosystems, Foster City) and the relative quantity was calculated. All samples were carried out in duplicates. A quantification during the data analysis was achieved by means of the dye SYBR Green. The amplification curves measured for the individual gene products were depicted graphically and evaluated in relation to the curve of the control gene. To quantitatively determine the target template, the average CT value (threshold cycle) was measured, i.e., the number of cycles within which the fluorescence of the reporter reaches a fixed threshold above the baseline values. Then, the difference (ΔCT) between the average CT values of the samples in the defined wells and those of the housekeeping genes, GADPH and β-actin, and then the difference (ΔΔCT) between the average ΔCT values of the samples for each target gene and the ΔCT value of the control sample for said target gene were calculated. This relative quantification value (also called fold difference), the amount, is expressed as $2^{-\Delta\Delta CT}$.

Agarose Gel Electrophoresis

PCR fragments were analyzed in a 2.0% (w/v) agarose gel in a horizontal electrophoresis. Depending on the gel size and desired agarose concentration, the required amount of agarose powder was weighed in an Erlenmeyer flask and the appropriate volume of 1× TBE buffer was added. To bring the agarose into solution, it was necessary to repeatedly bring the gel preparation to the boil in a microwave. An ethidium bromide solution was added to the hot gel solution up to a concentration of 0.5 mg/ml in the gel. The desired gel mold was closed on the open sides using adhesive tape and, depending on the desired separation path, one or two well-forming combs were placed in the gel mold. A spirit level was used to level the mold. The somewhat cooled agarose solution was poured into the prepared gel mold. The prepared agarose gel was placed into the electrophoresis apparatus. This was filled with 1×TBE buffer until the gel was completely covered. The samples to be loaded were admixed with 5× gel loading buffer, resulting in a 1× buffer concentration. The sample was mixed by carefully pipetting up and down and introduced into the formed wells of the gel. The applied sample volume was about 13 µl. The size of the fragments was determined by using a size marker. During electrophoresis, it was possible to observe the path covered by means of the bromophenol blue dye of the gel loading buffer. The electrophoresis was carried out at a voltage of 90 V for 4-5 hours.

Measurement of the Effect of Lactobin N on Oxidative Stress and DNA Damage

Leukocytes are of great value as a model for assessing oxidative stress and the modulation thereof. In vitro, the HL-60 promyelocytic leukemia cell line has been found to be very reliable for the analysis of NADPH oxidase activity. It can be increasingly proven that DNA is one of the most important targets of oxidative attacks. If repair mechanisms do not repair the oxidative DNA damage, this can have harmful consequences for the cells. Therefore, the effect of Lactobin N on oxidative DNA damage and oxidative stress in HL-60 cells was examined (Schupp N, Schmid U, Heidland A, Stopper H. Rosuvastatin protects against oxidative stress and DNA damage in vitro via upregulation of glutathione synthesis. Atherosclerosis 2008; 199: 278-287).

Cell Culture

The HL-60 (human promyelocytic leukemia cells) cell line (NIH, Washington, USA) was cultured in RPMI 1640 supplemented with 10% FBS, 1% L-glutamine, penicillin (100 units/ml) and 0.1 mg/ml streptomycin. The cells were seeded in a 6-well plate (Sarstedt Inc., Newton, USA) at a starting concentration of $5\times10^5$ cells/well, and untreated for 20-24 hours. Then, the cells were exposed to 100 mg/ml Lactobin N and 100 or 200 µM $H_2O_2$ for 30 minutes or 3 hours. $H_2O_2$ was used as the control for oxidative effects.

Flow Cytometric Analysis of Oxidative Stress 2,7-Dichlorodihydrofluorescein diacetate (H2DCF-DA) was used for detecting ROS production in the cells. The HL-60 cells were preincubated with 10 µM H2DCF-DA at 37° C. for 15 minutes; thereafter, the test substance was added. The cells were harvested und washed three times with PBS und 1% BSA. 5×10³ cells/sample were analyzed by flow cytometry using a FACS LSR I (Becton-Dickinson, Mountain View, Calif., USA).

Comet Assay

An alkaline version of the comet assay was carried out in accordance with Schupp et al. (Schupp N, Schmid U, Heidland A, Stopper H. Rosuvastatin protects against oxidative stress and DNA damage in vitro via upregulation of glutathione synthesis. Atherosclerosis 2008; 199: 278-287). The analysis comprised 50 randomly selected cells (25 per replicate slide) for each sample. The samples were analyzed using a fluorescence microscope (Labophot 2, Nikon, Germany) at 200× magnification using Komet 5 image analysis software (BFI Optilas, Germany). The percentage share of DNA in the tail (% tail DNA) was used for quantification of the migration of DNA.

Endotoxin Level and Neutralization Capacity of the Lactobin N

Endotoxins or lipopolysaccharides (LPS) are large (molecular weight: 200 to 1000 kDa), heat-resistant (up to 100° C.) molecules which form the most important structural components of the outer cell wall of Gram-negative bacteria. Endotoxin consists of a bioactive lipid part, called lipid A, covalently bonded to a hydrophobic heteropolysaccharide of variable length. Triggering of a signal transduction cascade leads to the binding of endotoxin to CD14 followed by the association with the protein MD2 and the transmembrane protein TLR4. This ultimately leads to the release of inflammatory cytokines, including IL-1β, TNF-α and IL-6, mainly released by immune cells such as macrophages and dendritic cells. Currently, the LAL test is the standard test for determining endotoxins in medicaments, biological products and medical devices. In general, three different LAL assays are used: gelation test, turbidimetric (increase in turbidity) and chromogenic (color development). (Guideline on Validation of the Limulus Amebocyte Lysate Test as an End-Product Endotoxin Test for Human and Animal Parenteral Drugs, Biological Products and Medical Devices. U.S. Dept. of Health & Human Services, FDA, December 1987; Interim Guidance for Human and Veterinary Drug Products and Biologicals. U.S. Department of Health & Human Services, FDA, Jul. 15, 1991; "Bacterial Endotoxins Test." In The U.S. Pharmacopeia, 25th revision, 12601 Twinbrook Parkway, Rockville, Md. 20852). For the quantification of endotoxins, use was made of the LAL test with kinetic and chromogenic detection.

Endotoxin Detection and Quantification Using Endosafe® Endochrome-K™ Limulus Amebocyte Lysate (LAL)

The LAL test (Charles River Endosafe, Charleston, S.C., USA) was used in accordance with the guidelines of the U.S. Food and Drug Administration (FDA) and is recommended for the quantification of endotoxins. A solution of Lactobin N was used (stock solution of 1 mg/ml prepared 1:1 and 1:2 (and 1:4)). First, 0.1 ml of Lactobin N or 0.1 ml of Lactobin N with blood from healthy volunteers were each pipetted into a well of a microtiter plate. Plasma (2 ml) derived from heparin blood from volunteers (n=15) was first incubated with 2 ml of endotoxin standard (50 EU/ml) at 37° C. and 5% $CO_2$ for 24 hours. Thereafter, 100 µl were further incubated with 100 µl of Lactobin N at 37° C. and 5% $CO_2$ for three further hours. A dilution with $H_2O$ (1:50) was carried out and the solution was inactivated by 5 minutes at 75° C. in a water bath. The samples were pipetted into a 96-well plate together with the lysate kit (limulus amebocyte lysate, Charles River, Charleston, S.C., USA) and measured at 405 nm using an Elisa reader (Endoscan 5, Charles River) and analyzed in accordance with the recommendations from the manufacturer (limulus amebocyte lysate). To determine suitable method parameters, the guidelines from the manufacturer were followed. The endotoxin control samples consisted of endotoxin standard series composed of positive and negative controls. For the endotoxin standard series, a fresh set of dilutions was prepared from the endotoxin stock solution for each test. During the assay, the increase in absorbance of the tube or of the microtiter plate was monitored by a suitable measurement instrument. The measurement instrument measures the time required until the absorbance has distinctly risen above the background, typically from 0.050 to 0.200 OD units. Said time is referred to as the onset time. The software of the measurement instrument automatically creates a log/log correlation of the onset time of each standard with the associated endotoxin concentration. The features of the standard curve are displayed and evaluated in order to establish whether the analysis is valid. The polynomial regression is calculated for the user using the Endoscan-V software.

Plasma (2 ml) from heparin blood from test subjects (n=15) was incubated with 2 ml of endotoxin standard (50 EU/ml) at 37° C. and 5% $CO_2$ for 24 hours. Thereafter, preparation 1 (100 µl) was incubated with 100 µl of the dissolved test substances at 37° C. and 5% $CO_2$ for a further 3 hours. After 3 hours, a 1:50 dilution with $H_2O$ was prepared and inactivated for 5 min in a water bath at 75° C. The samples were pipetted together with lysate kit into a 96-well plate. The plate was subsequently measured and evaluated in an Elisa reader.

What were examined were the saved materials from altogether 48 patients with histologically defined colorectal carcinoma (CRC), who had previously been subjected to a curative surgical resection in the Chirurgische Klinik [surgical clinic] of the Universitätsklinikum Würzburg [University Hospital of Würzburg] (TNM system: Union International Contre le Cancer, UICC stages I-IV, cf. FIG. 2). For each UICC stage, the carcinomas came from 12 patients; they were categorized with respect to their localization, their degree of wall infiltration (T) and lymph node metastasis (N) and presence of a distant metastasis (M) in accordance with the current TNM system, and grading (G), and archived together with the patient characteristics (age and gender) and the follow-up in the tumor database. Tumor aftercare examinations took place at regular intervals for the patients in accordance with the guidelines of the Bayerische Tumorzentren [Bavarian tumor centers]. The venous blood collected before the surgical procedure and also both the intraoperatively removed tumor tissue samples and normal colon tissue which had arisen during the surgical resection following preoperative consent of the patients were saved and all data were accurately documented. Peripheral blood samples from healthy individuals (n=12) served as controls.

It was intended that the examinations of the blood monocytes of an individual patient be used to discover indicators for inflammatory or, perhaps, therapy-related anti-inflammatory processes which are caused by the tumor disease and which could possibly be influenced by the pharmaceutical composition. The concentration ranges, both of the individual components of the pharmaceutical composition and of the combination thereof in the corresponding tumor cell suspensions, had been approximately matched with the currently established dosages of the colostrum preparation Lactobin® in the various clinical studies, or the recommended dosages for vitamin D3. The measured values were transformed by computational methods and depicted graphically in the form of bar charts. For the data evaluation, use was made of the Mann-Whitney U test and Student's t test. Values where P<0.05 were considered statistically significant.

The colostrum preparation Lactobin® N comes from the company Dr. Wolz Zell GmbH, Marienthaler Strasse 3, 65366 Geisenheim (www.wolz.de). According to the information from the manufacturer, this is a concentrate (in powder form) of bovine origin (New Zealand cattle) which is natural, additive-free and manufactured from at least 200 individual colostra (large pool) and which is obtained as follows:
1. The crude colostrum is obtained from cows which have been separated from their herd in order to avoid a contamination with normal milk;
2. The crude colostrum is filtered and stored at 4-7° C.;
3. Various crude colostra from different farms are collected and stored at <12° C.;
4. The fat is removed in order to increase the shelf life of the product. This can be done using conventional methods;
5. The colostrum thus obtained is pasteurized at 72° C. for 15 seconds (in accordance with EU requirements);
6. The product is concentrated at temperatures of <55° C. by membrane filtration and vaporization;
7. A powder is manufactured by spray drying at a low temperature;
8. If necessary, the colostrum powder is admixed with other colostrum powders in order to reach the content values specified in Table 2.

This approach and especially the use of a pool of colostra ensure that the product can exhibit the consistent and uniform quality that is required. An example of the values of a particular batch of the colostrum powder according to the invention is shown by Table 3.

Typically, the colostrum powder comprises over 80% by weight of proteins, <2% by weight of fat, <11% by weight of lactose, <5% by weight of water, <0.2 µg/100 g vitamin D (average values). It contains not only cytokines, growth factors and enzymes, but also immunoglobulins (especially of the IgG1 class). For IgG (subclass IgG1), quantitative measured values are 21-24% by weight.

The colostrum powder according to the invention does not contain any preservatives or antioxidants, etc. Nevertheless, it is nonperishable for at least 24 months when stored properly.

According to the invention, vitamin D3 is then added to said colostrum powder. In the present case, a vitamin D3 preparation stabilized with cornstarch is added. To this end, vitamin D3 (cholecalciferol) and DL-α-tocopherol are dissolved in liquefied and partially hydrogenated soybean oil and processed with an aqueous solution of gelatin and sucrose to give an emulsion. Said emulsion is sprayed into cornstarch. The powder obtained is separated from the excess starch, dried and packaged. The powder obtained contains vitamin D3, 2.5 mg/g; DL-alpha-tocopherol, 2 mg/g; partially hydrogenated soybean oil, 75 mg/g; hydrolyzed animal protein, 380 mg/g; sucrose, 380 mg/g; cornstarch, 160.5 mg/g.

To prepare a preparation according to the invention, the above-described colostrum powder (preferably Lactobin N) was admixed with an appropriate amount of the vitamin D3-containing powder, achieving the inventive concentration of vitamin D3. A mixing ratio used according to the invention was 0.2 mg of the vitamin D3-containing powder per gram of colostrum powder (0.2 mg/g). This yielded 0.5 µg of vitamin D3/g of ready-made preparation for the samples. A recommended daily dose is 10 g of ready-made preparation, i.e., 5 µg of vitamin D3. The ready-made preparation (composed of Lactobin N) was used in the experiments when a combination of Lactobin N and vitamin+D3 is specified (e.g., "Lact.+Vit. D3" in Table 1 or "Lact N+Vit D3" in the figures). Similarly, only the vitamin D3 preparation was used when the samples were treated only with vitamin D3 (e.g., "Vit. D3" in Table 1). Controls without vitamin D3 were treated with Lactobin N (also abbreviated as "Lact N").

Results:

Effects of the Individual Components and of the Combination on MNC and Tumor Cells of CRC Patients:

Monocytes play an important role as target cells and effector cells in antigen recognition and defense against infection. Situated thereon are defined patterns of functionally important surface antigens. If monocytes are activated, the pattern of surface antigens can change. The highly elevated total monocyte cell count in patients of early and advanced tumor stages (especially UICC stage III) was normalized with in vitro incubation with the colostrum preparation Lactobin® N. With coincubation with vitamin D3, it was possible to establish a significant synergistic effect for both monocytes from UICC stage I patients and UICC stage II patients (FACS analysis): it was possible to observe a similar behavior of the CD14-positive MNC from UICC stage I, II and III patients after incubation with individual components and the combination (significantly lowered in terms of a synergistic effect).

Analogously: Lowered expression of the CD68 gene in monocytes from the blood of patients of UICC stages I to IV (measurement by RT-qPCR) both with the individual components and with the combination (Lactobin® N vs. untreated control: UICC I and II: p<0.0001; UICC III: p<0.001 and Lactobin N+vitamin D3 vs. untreated control: UICC I-III: p<0.0001). Comparison of the individual components with the combination showed a synergism (p<0.01); in comparison with the individual components, the combination was again statistically significantly more effective (cf. FIG. 3).

In addition, as a crucial further indication of a normalized inflammatory response in the blood of CRC tumor patients, a decrease in the expression of the TLR4 gene in the cell culture preparations was established with the aforementioned coincubations in all tumor stages (UICC stages I-IV) (UICC I-II p<0.001, UICC III p<0.01) (again in terms of a synergism in comparison with the individual components) (cf. FIG. 4).

Furthermore, the drop in the gene expression profile for IGF 1 (apoptosis inhibitor) in the MNC of blood became distinctly apparent after a 12-hour incubation with Lactobin® N, vitamin D3 and the combination (Lactobin® N vs. untreated control: UICC I and II: p<0.001; UICC III: p=0.02 and Lactobin® N+vitamin D3 vs. untreated control: UICC I and II: p<0.001; UICC III: p=0.02). Comparison of the individual components with the combination showed a synergism in patients of UICC stages I-III (p<0.01) (cf. FIG. 5).

Figure 6:
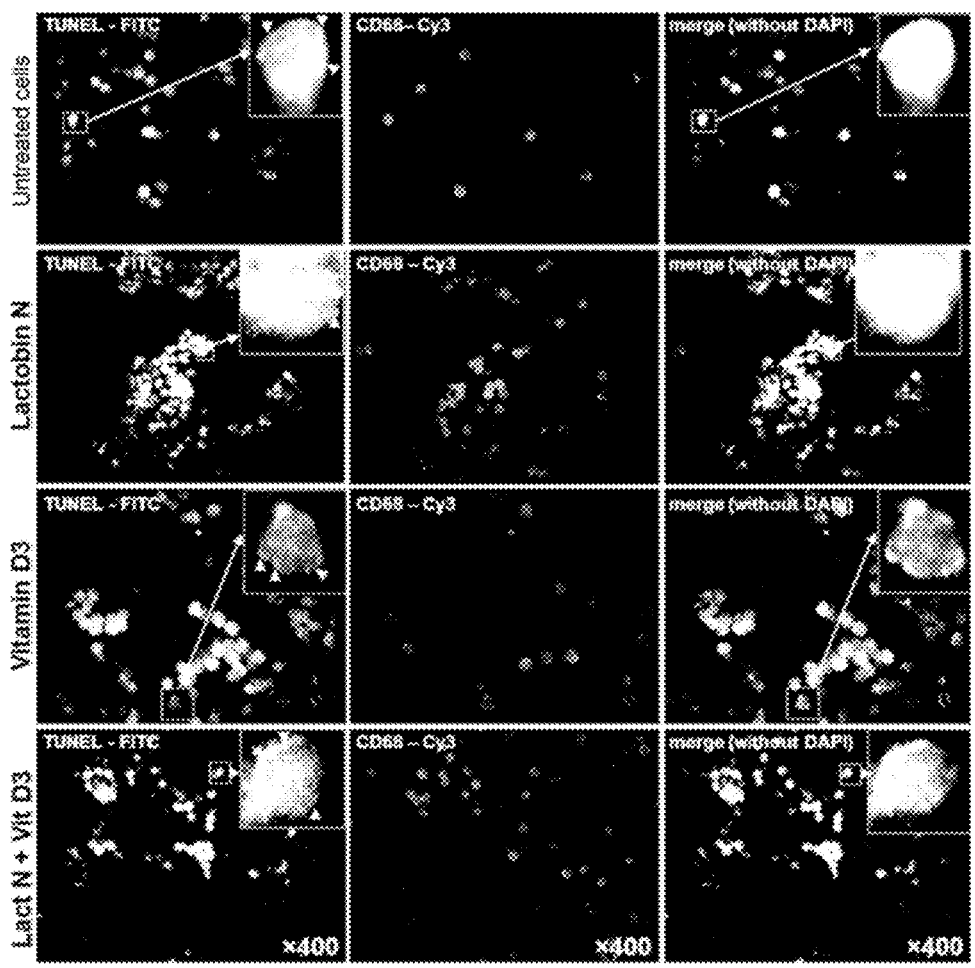
FIG. 6 shows Tunel stainings of CD68-positive MNC of mononuclear cells from CRC patients that have been isolated from cell culture and beforehand from blood (representative example—UICC II)

The results described above could be carried out on the basis of Tunel stainings of CD68-positive MNC of mononuclear cells from CRC patients that had been isolated from cell culture and beforehand from blood. They impressively show enhancedly apoptotic MNC from the blood of the CRC patients (cf. FIG. 6, representative example from UICC II patients). The findings described further above by means of gene expression analysis were confirmed by means of FACS for examined cells from patients of UICC stages I and II.

Lowered MNC in FACS analysis with Lactobin® N on its own and with the combination treatment (cf. FIG. 7).

The examinations of the peripheral blood monocytes were followed by the analysis of the tumor tissue, consisting of disintegrated cells (total fraction) from the tumor tissues (tumor cells and tumor-infiltrating macrophages and also further tumor-infiltrating immune cells). Enhanced apoptosis rates of tumor-infiltrating macrophages comparable to the rates already in the MNC removed from peripheral venous blood became apparent in the examined cells from the primary tumor tissues (cf. FIG. 8, representative example of UICC II).

Gene expression for CD68 was lowered in all tumor tissues (UICC stages I-IV) with incubation with Lactobin® N (Lactobin® N vs. untreated control: UICC I and II p<0.0001 and Lactobin N+vitamin D3 vs. untreated control: UICC I-III p<0.0001). The coincubation with vitamin D3 thus yielded synergistic effects (UICC stages I-III) (cf. FIG. 9).

In parallel to the lowered CD68 expression of the tumor-located macrophages, a drop in the gene expression of the macrophage receptor CD14 was also measured (Lactobin® N vs. untreated control: UICC I-III p<0.0001 and Lactobin® N+vitamin D3 vs. untreated control: UICC I-III p<0.0001). The addition of vitamin D3 thus led to synergistic effects (UICC stages I-III) (cf. FIG. 10).

Gene expression for TLR4 was lowered with Lactobin® N in parallel to CD14 expression (Lactobin® N vs. untreated control: UICC I-III p<0.001). The addition of vitamin D3 did not show any additional effects (UICC I-IV) (cf. FIG. 11).

For IGF1 expression, there was, in parallel to the aforementioned gene expressions in all tumor tissues (UICC stages I-IV), a consistently lowered expression profile with Lactobin® N (Lactobin® N vs. untreated control: UICC I-II p<0.001; UICC III p<0.01). The addition of vitamin D3 additionally showed slight synergistic effects (Lactobin® N+vitamin D3 vs. untreated control) (cf. FIG. 12).

It was possible to determine a lowered expression of the CD14 gene in MNC of CRC patients with incubation with the colostrum preparation Lactobin® N in all UICC stages (I-IV). Furthermore, it was possible to show an additional synergistic effect in the coincubation of Lactobin® N and vitamin D3 (cf. FIG. 13 and FIG. 14; measurements by means of RT-qPCR and FACS analysis).

The test for oxidative stress in HL-60 cells was carried out in order to rule out negative effects in the case of direct incubation of monocyte cells with Lactobin® N. Neither after a 30-minute nor after a 60-minute incubation was there a significant enhancement of the oxidative stress (cf. FIG. 15).

In the comet assay, in parallel to the aforementioned test for oxidative stress, no significant change in DNA damage in HL-60 cells was observed after a three-hour incubation with Lactobin® N (cf. FIG. 16).

In the LPS neutralization test, a distinct neutralization capacity was observed for Lactobin N (cf. FIG. 17).

The Luminex assay established further direct indications of a downregulated inflammatory response (IL-1β, IL-6, IFN-γ and TNF-α) in the MNC from CRC tumor patients in parallel to the downregulated gene expressions for CD68, CD14 and TLR4 in the cell culture preparations with the abovementioned (co)incubations in all tumor stages (UICC stages I-IV) (with coincubation: UICC stages I and II p<0.01) (Table 1).

DISCUSSION/CONCLUSIONS

From examinations of patients with solid tumors, there are increasingly indications of enhanced inflammatory reactions during progressive tumor disease. The cause and impacts of these inflammatory immune responses proceeding at an elevated base level have so far only been partly clarified. Despite enhancedly measurable inflammation parameters in the blood, what can be frequently observed is a clinical weakening of the tumor patient in his readiness to react to infectiological problems and to his tumor depending on its progression. In addition, there are now several studies concerning how the immune system of a tumor patient responds to a tumor at the cellular and molecular level (specific immune response against tumors, effector cell response, specific T-cell cytotoxicity, antibody-mediated defense against tumors). Prognostic predictions have so far been derived more from the infiltration density of particular immune defense cells in a solid tumor, which intrinsically appear quite conclusive. Against the background that a solid tumor such as, for example, a colorectal carcinoma (CRC) in progressive tumor growth enhancedly carries an inflammatory microenvironment (inflammatory cells and messenger substances) within itself and inflammatory parameters become increasingly measurable even in peripheral blood, a necessary therapeutic normalization and thus modulation of this overloaded inflammation response is imperative for the treatment of tumor diseases. This comes from the insight that a chronically enhanced inflammatory base activity reduces the ability for immunological engagement with a tumor and especially the specific defense thereagainst.

Dependent factors of an immunological engagement and especially indicators for inflammatory reaction processes caused by tumor diseases can be influenced by the pharmaceutical composition according to the invention, for example in CRC patients, and were therefore examined in tumor cells of the affected patients. Said patients exhibited an enhanced reactivity against lipopolysaccharides (LPS) and the presence of an overshooting inflammatory responsiveness.

The reactivity of the immune system of a patient against LPS, which comes from the break-up of Gram-negative pathogens (e.g., *Escherichia coli* and Enterococci) in blood and especially on mucosal surfaces, elicits typical cellular reaction patterns in the course of an inflammation response which is forming, as depicted in part in FIG. 1. FIG. 18 depicts the mechanism of action of the pharmaceutical composition according to the invention.

The enhanced triggering of an inflammatory response via the TLR4 signaling pathway thus represents a reaction pattern of said patients that is frequently encountered in daily clinical practice. TLR4, an evolutionarily highly conserved element of the inflammation response, is an ideal representative therefore and was therefore selected specifically and for the first time for the measurement of inflammatory events in a tumor patient.

TLR4 is (inter alia) expressed by monocytes and macrophages. The detection of this receptor, in this case especially in conjunction with the corresponding cell counts, is thus characteristic for a current or already undergone inflammation response to bacterial pathogens in a tumor patient, this—a generally overshooting reaction—being of great pathophysiological significance for the patient. His—as shown for the first time according to the invention in this manifestation—overloaded reaction to LPS flowing in from the gastrointestinal tract represents in this case a realistic clinical indicator.

Monocytes/macrophages go into "self-induced cell death" only under a certain signaling action, i.e., "on demand". The threshold for apoptosis induction in the cells in the case of tumor patients is—as could be shown according to the invention—shifted, since there are measurably inflated monocyte cell counts specifically in patients with increasing tumor load. It was possible to observe this phenomenon without clinically specifically identifiable signs of a bacterial or viral infectious disease being determinable at the same time. This shows that, in the course of the tumor progression and the increasing inflammation response, there were elevated threshold values for triggering apoptosis in the monocytes.

Lactobin® N and vitamin D3 have been used in medicine for some time. Among the numerous colostrum preparations available on the market, Lactobin® N has arguably the broadest base of preclinical and clinical data. It is notable for the high uniformity of its production batches, this being of greatest importance for such a highly complex mixture of active ingredients. In this connection, one finding comes from a clinical study with 40 abdominal surgery patients who were treated perioperatively with Lactobin® or with placebo. In this case, the patients treated with the colostrum preparation exhibit a statistically significantly lower LPS level in their serum, implying the intraenteral neutralization thereof (Edwin Bölke et al.: PREOPERATIVE ORAL APPLICATION OF IMMUNOGLOBULIN-ENRICHED COLOSTRUM MILK AND MEDIATOR RESPONSE DURING ABDOMINAL SURGERY. SHOCK, Vol. 17, No. 1, pp. 9-12, 2002). In this respect, the polyclonality of the anti-LPS specificities (anti-O-chain diversity) is crucial.

Ultimately, the anti-O-chain diversity is also responsible for the toxin neutralization not being subject to any resistance development. Colostrum production during the first days after birth conforms to the uninterrupted immunization of the mother animal, which is progressively exposed to the antigen spectrum of its environment, this additionally further contributing to an enhancement of diversity as a result of migration of the herd animals, on the one hand, and as a result of the pooling of on average more than 200 individual colostra for the production of one Lactobin batch. Furthermore, the LPS neutralization potential is additionally enhanced by the anti-lipid-A neutralization capacity via the lactoferrin likewise present in the Lactobin®. Against this entire background, the execution of the already mentioned pharmacodynamics study by Waaga-Gasser et al. (A. M. Waaga-Gasser et al.: Oral immunoglobulin induces mononuclear cell apoptosis in patients suffering from idiopathic chronic pain syndrome: Results from a pilot study. International Journal of Clinical Pharmacology and Therapeutics, Vol. 47—No. 7/2009, pp. 421-433) appears plausible, in which study it was possible to show, especially by means of the TUNEL technique, the induction of the restoration of normal apoptosis conditions by Lactobin® N in parallel to making better the clinical symptoms of the treated patients suffering from pain.

Vitamin D has, in vitro, a multiplicity of effects which point to an immunomodulatory action. It is of particular interest that it was not possible to detect any immunosuppressive action in clinical trials. In a clinical study on CRC patients, a dependence of the 25-hydroxy D serum level had been detected (Stubbins R E et al.: 2012. Using components of the vitamin D pathway to prevent and treat colon cancer. Nutrition Reviews 70(12): 721-729).

When ingested orally, the pharmaceutical composition according to the invention brings about further pharmacodynamic processes at the intestinal mucosa boundary by means of the MALT system (mucosa-associated lymphatic tissue) located there. In this local subsegment of the immune system, the engagement with environmental pathogens takes place, with resulting overshooting reactions of activated peripheral monocytes being restored to the normal level via a preparation-related induction of apoptosis. In tumor patients, the inflammatory responsiveness is therefore already regulated locally, this being expressed in normalized monocyte counts, normalized CD14 and TLR4 expression and the restored IGF1 profiles.

The action of Lactobin® N beyond the gastrointestinal tract on infiltrated immunocompetent cells in the tumor tissue was, compared with monocytes in peripheral venous blood, found accordingly in all tumor stages, and this shows that the overloaded inflammatory microenvironment proceeding from monocytic cells which had infiltrated the tumor tissue can be downregulated by administration of Lactobin® and vitamin D3.

This clearly shows that, with a normalized systemically measurable inflammation response and a suppressed inflammatory microenvironment in the tumor tissue, immunological tumor defense mechanisms can proceed much more effectively.

The present examination results represent an exceptionally solid view of the reaction processes in tumor patients, more particularly intestinal cancer patients (CRC). This is shown by the results of the presently reported efficacy examination with Lactobin® N/vitamin D3 of human tumor cells and blood-located inflammatory cells. Particularly the synergistic effects in the case of combined use are significant for patients with colorectal carcinoma, not only for a primary prevention, but also for a secondary prevention after radical tumor surgery to increase the T effector cell response for occult distant metastases (minimal residual disease after radical tumor resection).

The described uniformity of the production of Lactobin® and the resulting homogeneity of the production batches is of fundamental importance for the validity of the analytical, preclinical and clinical data in relation to the product.

TABLE 1

Cytokine production by MNC after incubation with Lactobin ® N, vitamin D3, Lactobin ® N + Vit D3

| | | IL-1β pg/ml | IL-6 pg/ml | IFN-γ pg/ml | TNF-α pg/ml | IL-12 pg/ml | IL-10 pg/ml | IL-13 pg/ml | IGF-1 ng/ml |
|---|---|---|---|---|---|---|---|---|---|
| Control (n = 6) | Cells with no additive | 4.7 ± 0.4 | 3.1 ± 0.6 | 12.6 ± 2.3 | 62.1 ± 10.3 | 47.8 ± 6.5 | 27.5 ± 4.2 | 43.3 ± 9.3 | 93.4 ± 6.3 |
| | Lact N | 4.5 ± 0.6 | 3.0 ± 0.2 | 12.3 ± 3.1 | 62.2 ± 14.2 | 49.1 ± 7.1 | 27.8 ± 4.7 | 44.1 ± 11.2 | 91.4 ± 5.4 |
| | Vit D3 | 4.8 ± 0.1 | 3.3 ± 0.3 | 12.8 ± 4.7 | 62.6 ± 10.7 | 47.7 ± 8.3 | 27.9 ± 5.8 | 43.6 ± 10.6 | 90.3 ± 4.7 |
| | Lact + Vit D3 | 4.5 ± 0.4 | 3.0 ± 0.1 | 12.1 ± 5.2 | 62.2 ± 10.3 | 41.1 ± 6.9 | 28.1 ± 4.8 | 44.9 ± 9.5 | 89.1 ± 4.1 |

TABLE 1-continued

Cytokine production by MNC after incubation with Lactobin ® N, vitamin D3, Lactobin ® N + Vit D3

|  |  | IL-1β pg/ml | IL-6 pg/ml | IFN-γ pg/ml | TNF-α pg/ml | IL-12 pg/ml | IL-10 pg/ml | IL-13 pg/ml | IGF-1 ng/ml |
|---|---|---|---|---|---|---|---|---|---|
| UICC I (n = 6) | No additive | 60.1 ± 7.8 | 99.2 ± 10.8 | 71.8 ± 6.3 | 120.1 ± 6.5 | 97.6 ± 8.3 | 11.9 ± 6.4 | 23.0 ± 7.3 | 195.2 ± 20.5 |
|  | Lact N | 21.9 ± 7.4 | 38.8 ± 9.4 | 42.3 ± 7.5 | 72.6 ± 7.4 | 61.9 ± 8.1 | 24.7 ± 6.2 | 33.9 ± 8.2 | 122.3 ± 22.6 |
|  | Vit D3 | 42.5 ± 6.8 | 98.7 ± 9.5 | 58.5 ± 9.3 | 83.6 ± 6.3 | 74.9 ± 9.6 | 18.3 ± 7.4 | 30.1 ± 8.9 | 148.6 ± 24.1 |
|  | Lact + Vit D3 | 11.3 ± 6.3 | 41.9 ± 7.4 | 30.4 ± 7.6 | 64.8 ± 7.3 | 51.0 ± 9.5 | 26.9 ± 8.3 | 42.9 ± 8.4 | 95.3 ± 19.3 |
| UICC II (n = 6) | No additive | 58.1 ± 8.6 | 113.2 ± 5.8 | 103.9 ± 11.6 | 223.4 ± 8.4 | 113.5 ± 12.6 | 10.4 ± 3.6 | 17.1 ± 9.7 | 261.7 ± 27.3 |
|  | Lact N | 20.8 ± 7.5 | 76.3 ± 6.4 | 57.3 ± 10.7 | 121.7 ± 10.2 | 69.4 ± 10.4 | 20.9 ± 4.2 | 36.6 ± 9.5 | 186.7 ± 32.3 |
|  | Vit D3 | 34.8 ± 7.9 | 102.8 ± 8.9 | 77.3 ± 11.1 | 169.1 ± 11.1 | 80.1 ± 12.8 | 18.1 ± 3.1 | 27.9 ± 10.3 | 213.4 ± 33.6 |
|  | Lact + Vit D3 | 15.6 ± 6.1 | 81.6 ± 5.9 | 46.2 ± 8.6 | 86.3 ± 9.3 | 59.6 ± 9.7 | 23.9 ± 3.8 | 39.3 ± 7.4 | 101.8 ± 47.2 |
| UICC III (n = 6) | No additive | 175.0 ± 10.1 | 95.4 ± 11.7 | 258.9 ± 8.3 | 362.8 ± 10.7 | 305.7 ± 21.8 | 7.8 ± 4.3 | 10.1 ± 4.9 | 334.8 ± 30.4 |
|  | Lact N | 147.5 ± 9.5 | 73.5 ± 9.4 | 165.0 ± 10.9 | 293.1 ± 11.4 | 175.3 ± 23.6 | 20.1 ± 3.5 | 31.4 ± 4.5 | 249.9 ± 44.2 |
|  | Vit D3 | 169.4 ± 14.7 | 91.7 ± 7.6 | 215.9 ± 9.4 | 331.5 ± 11.9 | 214.7 ± 19.4 | 17.9 ± 7.8 | 26.1 ± 5.8 | 299.1 ± 61.1 |
|  | Lact + Vit D3 | 118.1 ± 7.8 | 76.7 ± 4.3 | 150.1 ± 10.8 | 264.7 ± 10.5 | 92.9 ± 19.7 | 22.9 ± 6.3 | 35.8 ± 6.7 | 183.5 ± 33.2 |
| UICC IV (n = 6) | No additive | 372.8 ± 15.6 | 213.2 ± 11.1 | 335.7 ± 9.5 | 423.4 ± 9.3 | 532.2 ± 14.2 | 5.0 ± 3.1 | 9.5 ± 5.3 | 895.6 ± 55.2 |
|  | Lact N | 351.9 ± 11.9 | 201.3 ± 10.9 | 268.7 ± 9.0 | 400.7 ± 10.6 | 461.3 ± 11.3 | 10.1 ± 3.8 | 18.9 ± 6.9 | 871.4 ± 38.5 |
|  | Vit D3 | 369.9 ± 9.4 | 213.1 ± 8.6 | 292.5 ± 9.4 | 413.1 ± 11.5 | 499.9 ± 16.9 | 7.9 ± 4.2 | 9.1 ± 6.4 | 896.4 ± 58.2 |
|  | Lact + Vit D3 | 351.8 ± 10.4 | 205.4 ± 9.3 | 205.8 ± 10.1 | 402.1 ± 10.9 | 432.1 ± 14.2 | 18.6 ± 4.9 | 18.1 ± 6.1 | 873.5 ± 66.1 |

TABLE 2

| Total shares: | |
|---|---|
| Protein | 70-90% by weight or >80% by weight |
| Fat | <2% by weight |
| Moisture | <5% by weight |
| Lactose | <11% by weight |
| Special constituents already present in the total shares: | |
| Immunoglobulin G (measured by HPLC) | >20% by weight (based on protein share) |
| Lactoferrin | 1-5% by weight |
| Further constituents: | |
| Vitamin D | <0.2 µg/100 g |
| Iron | <2 mg/100 g |

TABLE 3

| Total shares: | |
|---|---|
| Protein | 80.7% by weight |
| Fat | 1.5% by weight |
| Moisture | 3.9% by weight |
| Ash | 5.3% by weight |
| Lactose | 8.6% by weight |
| Special constituents already present in the total shares: | |
| Immunoglobulin G (measured by HPLC) | 21.1% by weight |
| Lactoferrin | 3.1% by weight |
| Further constituents: | |
| Vitamin D | <0.2 µg/100 g |
| Vitamin A | 20 µg/100 g |
| B2 | 578 µg/100 g |
| B6 | ND µg/100 g |
| B12 | 17.8 µg/100 g |
| C | 1 mg/100 g |
| E | 164 µg/100 g |
| Folic acid | 230 µg/100 g |
| Iron | 0.8 mg/100 g |
| Physical properties: | |
| Density | 0.5 g/ml |

CITED LITERATURE

Cited Patent Literature

EP 0917467 A1
EP 2121002 A1

Cited Nonpatent Literature

Cesarone, M. R., Belcaro, G., Di Renzo, A., Dugall, M., Cacchio, M., Ruffini, I., Pellegrini, L., ( . . . ), Vinciguerra, G.: "Prevention of influenza episodes with colostrum compared with vaccination in healthy and high-risk cardiovascular subjects: the epidemiologic study in San Valentino" in: Clinical and Applied Thrombosis/Hemostasis 13(2)/2007, pp. 130-136

Tacket C O, Binion S B, Bostwick E, Losonsky G, Roy M J, Edelman R.: "Efficacy of bovine milk immunoglobulin concentrate in preventing illness after *Shigella flexneri* challenge". American Journal Tropical Medicine Hygiene 47(3)/1992, pp. 276-83

H I Huppertz et al.: "Bovine Colostrum Ameliorates Diarrhea in Infection with Diarrheagenic *Escherichia coli*, Shiga Toxin-Producing *E. coli*, and *E. coli* Expressing Intimin and Hemolysin". J. Ped. Gastroenterol. Nutr. 29: 452-456 1999

Uruakpa F O, Ismond M A H, Akobundu E N T: "Colostrum and its benefits: a review". Nutrition Research 22/2002, pp. 755-67

Harmsen, Martin C. et al.: Antiviral effects of plasma and milk proteins: lactoferrin shows potent activity against both human immunodeficiency virus and human cytomegalovirus replication in vitro. Journal of Infectious Diseases, Vol. 172, No. 2, 1995, pp. 380-388

Park, Ji-Hye et al.: An antimicrobial protein, lactoferrin exists in the sweat: proteomic analysis of sweat. Experimental Dermatology, Vol. 20, No. 4, 2011, pp. 369-371

W. G. Struff and G. Sprotte: Bovine colostrum as a biologic in clinical medicine: a review. International Journal of Clinical Pharmacology and Therapeutics, Vol. 45—No. 4/2007 (193-202)

W. G. Struff and G. Sprotte: Bovine colostrum as a biologic in clinical medicine: a review—Part II: International Journal of Clinical Pharmacology and Therapeutics, Vol. 46—No. 5/2008 (211-225)

A. M. Waaga-Gasser, M. Gasser, M. Stock, M. Grimm and G. Sprotte: Oral immunoglobulin induces mononuclear cell apoptosis in patients suffering from idiopathic chronic pain syndrome: results from a pilot study. International Journal of Clinical Pharmacology and Therapeutics, Vol. 47—No. 7/2009 (421-433)

Edwin Bölke, Peter M. Jehle, Frieder Hausmann, Armin Däubler, Heidemarie Wiedeck, Gerald Steinbach, Martin Storck and Klaus Orth: PREOPERATIVE ORAL APPLICATION OF IMMUNOGLOBULIN-ENRICHED COLOSTRUM MILK AND MEDIATOR RESPONSE DURING ABDOMINAL SURGERY. SHOCK, Vol. 17, No. 1, pp. 9-12, 2002

Florian Fitzal, Ildikó Racz, János Hamar, Heinz Redl and Soheyl Bahrami: Immunoglobulin Enriched Colostral Milk Reduces Gut-Derived Endotoxemia in a Rat Hemorrhage Model. European Journal of Trauma, 2001, pp. 257-263

N. ROOS, S. MAHÉ, R. BENAMOUZIG, H. SICK, J. RAUTEREAU AND D. TOMÉ: 15N-Labeled Immunoglobulins from Bovine Colostrum Are Partially Resistant to Digestion in Human Intestine. The Journal of Nutrition, 1995, pp. 1238-1244

R. Lissner, P. A. Thürmann, G. Merz and H. Karch: Antibody reactivity and fecal recovery of bovine immunoglobulins following oral administration of a colostrum concentrate from cows (Lactobin) to healthy volunteers. International Journal of Clinical Pharmacology and Therapeutics., Vol. 36, No. 5—1998 (239-245)

Stubbins R E, Hakeem A, Nunez N P 2012. Using components of the vitamin D pathway to prevent and treat colon cancer. Nutrition Reviews 70(12): 721-729

Manson J E. 2011. Vitamin D and Prevention of Cancer—Ready for Prime Time?. NEJM 364(15): 1385-87

Pietschmann P. et al. 2003. Bedeutung von Vitamin D im Immunsystem [Significance of vitamin D in the immune system]. J Mineral Stoffwechsel 10(3): 13-15

BMJ Research. Association between pre-diagnostic circulating vitamin D concentration and risk of colorectal cancer in European populations: a nested case-control StudyBMI/OnlineFirst/bmj.com Haussler M R et al. Vitamin D receptor: molecular signaling and actions of nutritional ligands in disease prevention. Nutritional Reviews 2008; 66: 98-112

A. M. Keech: Peptide Immunotherapy—Colostrum—A Physician's Reference Guide. AKS Publishing 2010

Schupp N, Schmid U, Heidland A, Stopper H. Rosuvastatin protects against oxidative stress and DNA damage in vitro via upregulation of glutathione synthesis. Atherosclerosis 2008; 199: 278-287 Guideline on Validation of the Limulus Amebocyte Lysate Test as an End-Product Endotoxin Test for Human and Animal Parenteral Drugs, Biological Products and Medical Devices. U.S. Dept. of Health & Human Services, FDA, December 1987

Interim Guidance for Human and Veterinary Drug Products and Biologicals. U.S. Department of Health & Human Services, FDA, Jul. 15, 1991

"Bacterial Endotoxins Test." In The U.S. Pharmacopeia, 25th revision, 12601 Twinbrook Parkway, Rockville, Md. 20852

The invention claimed is:

1. A method of treating a colorectal carcinoma in a human in need thereof consisting essentially of administering to said human in need thereof a therapeutically effective amount of cattle colostrum and vitamin D to effectively treat the colorectal carcinoma in said human in need thereof.

2. The method according to claim 1, which reduces lipopolysaccharide-triggered inflammation.

3. The method according to claim 1, wherein the vitamin D is cholecalciferol.

4. The method according to claim 1, wherein the therapeutically effective amount of cattle colostrum and vitamin D is administered at a daily dose of 5 g-50 g.

5. The method according to claim 1, wherein the therapeutically effective amount of cattle colostrum and vitamin D contains about 0.00001%-0.5% by weight of vitamin D.

6. The method according to claim 1, wherein the cattle colostrum is present as a concentrate or powder.

* * * * *